US012478555B2

(12) United States Patent
Luo

(10) Patent No.: US 12,478,555 B2
(45) Date of Patent: Nov. 25, 2025

(54) LIQUID STORAGE CONTAINER FOR A HUMIDIFIER

(71) Applicant: DCSTAR INC, New York, NY (US)

(72) Inventor: David Luo, New York, NY (US)

(73) Assignee: DCSTAR INC, New York, NY (US)

( * ) Notice: Subject to any disclaimer, the term of this patent is extended or adjusted under 35 U.S.C. 154(b) by 0 days.

(21) Appl. No.: 18/416,120

(22) Filed: Jan. 18, 2024

(65) Prior Publication Data

US 2025/0235382 A1 Jul. 24, 2025

(51) Int. Cl.
*A61M 16/10* (2006.01)
*A61J 1/16* (2023.01)
*A61M 16/16* (2006.01)

(52) U.S. Cl.
CPC .............. *A61J 1/16* (2013.01); *A61M 16/109* (2014.02); *A61M 16/16* (2013.01); *A61J 2200/42* (2013.01); *A61M 2205/3368* (2013.01); *A61M 2205/3653* (2013.01)

(58) Field of Classification Search
CPC . A61M 16/109; A61M 16/16; F24F 2006/008
See application file for complete search history.

(56) References Cited

U.S. PATENT DOCUMENTS 4,098,853 A * 7/1978 Brown ................ A61M 16/167 261/DIG. 65
2004/0050386 A1* 3/2004 Levine ................ A61M 16/167 128/203.16
2006/0055069 A1* 3/2006 DiMatteo .............. A61M 16/16 261/DIG. 65
2008/0302361 A1* 12/2008 Snow .................. A61M 16/109 128/202.27
2012/0097163 A1* 4/2012 Potharaju ............ A61M 16/109 128/203.26
2012/0146251 A1* 6/2012 Heine ............... A61M 16/1075 261/119.1
2014/0131904 A1* 5/2014 Tang ................... A61M 16/022 261/157
2015/0202402 A1* 7/2015 Kat ................... A61M 16/0066 128/203.27
2016/0228671 A1* 8/2016 Jackson .............. A61M 16/109
2018/0333556 A1* 11/2018 Ormrod ............ A61M 16/0051
2019/0298964 A1* 10/2019 Bayer ................... A61M 16/16
2019/0321580 A1* 10/2019 Kirchberger ...... A61M 16/0066
2022/0016383 A1* 1/2022 Workman ............ A61B 5/0826
2022/0016384 A1* 1/2022 Verma ................. A61M 16/109

FOREIGN PATENT DOCUMENTS

EP 2848277 A1 * 3/2015 .......... A61M 16/109
WO WO-2014138804 A1 * 9/2014 ........... A61B 5/0816

* cited by examiner

*Primary Examiner* — Kathryn E Ditmer
(74) *Attorney, Agent, or Firm* — HSML P.C.

(57) ABSTRACT

A liquid storage container to heat a certain volume of liquid. The liquid storage container includes a top cover, a middle layer, and a bottom part. The connection between the top cover and the bottom part is configured to be fully detachable. The top cover has at least a partial platform. The middle layer has a stopping element and a sealing element. The stopping element and a part of the sealing element are configured to connect to the bottom part and form a seal. A part of the sealing element is further configured to come into contact with and seal against the platform of the top cover. Together, they form a chamber to accommodate a certain volume of liquid. The bottom part has a heating plate to conduct heat.

16 Claims, 29 Drawing Sheets

LIQUID STORAGE CONTAINER FOR A HUMIDIFIER

TECHNICAL FIELD

This disclosure relates to one or more of the treatments and improvements of respiratory-related diseases. Specifically, this disclosure pertains to the usage of medical equipment as well as its production and manufacturing.

BACKGROUND

Sleep Apnea Syndrome (SAS), also known as Sleep Apnea-Hypopnea Syndrome, typically refers to the occurrence of more than 30 episodes of apneas and hypopneas per 7 hours of sleep each night, or a Sleep Apnea Hypopnea Index (AHI) of greater or equal to 5 events per hour. Long-term sleep apnea may be accompanied by decreased sleep quality, increased nocturia, dry mouth and headaches upon waking, decreased concentration and increased fatigue during the day, and reduced memory, as well as complications such as coronary heart disease, hypertension, and stroke, which seriously endanger human health. Based on different pathogenic mechanisms, it is divided into Obstructive Sleep Apnea Syndrome (OSAS), Central Sleep Apnea Syndrome (CASA), and Mixed Sleep Apnea Syndrome (MSAS). Most patients with obstructive sleep disorders typically use CPAP machines for home treatment.

Positive pressure ventilation therapy delivers breathable gas with pressure into the patient's airway through an airflow generator to prop open or flush away the patient's closed airway, achieving therapeutic purposes. Positive pressure ventilation therapy typically involves an airflow generator, liquid storage container, air delivery tubing, patient interface, and data monitor. In the air delivery process, the liquid storage container is an important component. Pressurized gas flows out from the airflow generator, passes through the liquid storage container and carries liquid molecules from within the chamber, and then enters the patient's oral and nasal airways. This prevents the long-term delivery of dry pressurized airflow to the patient's oral and nasal airways, which could cause dryness and discomfort in the oral pharynx and nasal mucosa, irritate the respiratory mucosa, cause inflammatory responses, or make respiratory secretions viscous, thereby increasing the burden on the throat and reducing the patient's compliance with treatment. However, the top covers and bottom parts of most liquid storage containers on the market, to prevent part loss, have non-detachable hinges as their connection method. Non-detachable hinges are usually difficult to clean and can easily cause accidents where patients' fingers are pinched during use, or the instability of the top cover's center of gravity may pull the entire assembly backward, leading to the liquid storage container tipping over. A few removable hinges, due to structural requirements, have thinner wall thicknesses at the hinge or smaller areas at the hinge, making them prone to breaking during disassembly. In addition, most liquid storage containers on the market typically use a silicone ring clamped in the middle of the top covers and bottom parts for sealing. To ensure that the silicone ring can effectively seal at a fixed position, the top cover and the bottom part usually have corresponding platforms to clamp the silicone ring. Although the design of platforms ensures overall functionality, it increases production costs: the obstruction by platforms prevents direct demolding by machines, adding to the production steps and increasing the overall production costs.

SUMMARY

Therefore, to address the aforementioned shortcomings, it is necessary to provide a liquid storage container that is both convenient for use and production, which is not only easy for the patient to use and clean but also simplifies the production process and reduces the overall production costs. Based on functionality, the liquid storage container is divided into three parts: the top cover, the middle layer, and the bottom part. The top cover and the bottom part have the same functions as a normal liquid storage container, with the bottom part capable of storing a certain volume of liquid, and the top cover fixedly connected to the bottom part to form a complete unit. Particularly, the design of the middle layer, combined with the platform and the silicone ring, allows the middle layer to achieve an overall seal of the liquid storage container without relying on the platform that hinders production, making the design and production of the top cover and the bottom part simpler.

In an embodiment, a liquid storage container to moisten pressurized breathable gas delivered to airways is provided. When the liquid storage container and an airflow generator are in an operational position, the liquid storage container can supply heat to liquid within a chamber. The liquid storage container includes: a top cover that is configured to engage with a bottom part through a snap-fit and to sealably connect to a middle layer, forming a detachable whole. The top cover includes a first opening formed by a continuous wall. The first opening corresponds to a second opening of a bottom part. The continuous wall includes an intake port and an exhaust port configured to be in communication with the airflow generator. Pipes extend from the intake port and the exhaust port respectively. The top cover further includes a fastener and a clip extending from the wall at the first opening to secure the bottom part, and a platform that contacts the middle layer. At least one fastener is located at a front end of the top cover, and at least one clip is located at a rear end of the top cover. Both the fastener and the clip are configured to jointly connect to the bottom part to limit movement of the top cover. The platform is configured to prevent the displacement of a middle layer and to form a seal.

The liquid storage container also includes a middle layer that is configured to be detachably connectable to the bottom part, and the middle layer includes a stopping element with a perimeter of an outer edge not smaller than a second opening of the bottom part, and a sealing element that contacts the top cover and the bottom part, and the stopping element is configured to contact an end surface of the second opening of the bottom part to prevent the middle layer from descending.

The liquid storage container also includes a bottom part that includes the second opening that fits with the top cover, and at least one protrusion at a front end of the bottom part for engaging with the fastener of the top cover, and at least one protrusion located at a rear end of the bottom part to connect to the clip of the top cover. The bottom part also includes an integrally formed wall, and a heating plate. The heating plate is configured to conduct heat.

In an embodiment, a horizontal plane in which the first opening of the top cover and the second opening of the bottom part are located is parallel. The first opening and the second opening are not in contact.

In an embodiment, the platform of the top cover that contacts the middle layer is either continuous or noncontinuous.

In an embodiment, the stopping element of the middle layer has at least a part of a perimeter of an outer edge not smaller than a perimeter of inner edge of the second opening of the bottom part.

In an embodiment, the bottom part includes a locator, which is in the form of a protrusion, a groove, a magnet or a contour.

In another embodiment, a liquid storage container is provided. The liquid storage container is to moisten pressurized breathable gas delivered to airways. When the liquid storage container and an airflow generator are in an operational position, the liquid storage container can supply heat to liquid within a chamber, and the liquid storage container includes: a top cover which is configured to engage with a bottom part through a snap-fit connection and to sealably connect to the middle layer, forming a detachable whole. The top cover includes a continuous wall and a first opening which corresponds to the bottom part. The continuous wall includes an intake port and an exhaust port configured to be in communication with the airflow generator.

Pipes extend from the intake port and the exhaust port respectively. The top cover further includes a fastener and clip extending from the wall at the first opening to secure the bottom part, and a platform that contacts a middle layer. The intake port and the exhaust port are on a same plane, and the pipes extending from the intake port and the exhaust port are parallel to each other, and the pipes extending from the intake port include a first section and a second section. The first section and the second section are not parallel to each other. The second section extends towards the bottom part and is perpendicular to a horizontal plane, and a length of the second section is shorter than a length of the first section.

The middle layer is configured to be detachably connectable to the bottom part, and seals the top cover and the bottom part.

The bottom part includes a second opening that fits with the top cover, at least one receiving part at a front end of the bottom part for engaging with the fastener of the top cover, and at least one receiving part at a rear end of the bottom part to connect to the clip of the top cover. The bottom part includes an integrally formed wall and a heating plate configured to conduct heat. The contact area of the heating plate with the wall of the bottom part is not less than 66 $mm^2$.

In an embodiment, an end surface of the first opening of the top cover is on a horizontal plane, and an end surface of the second opening of the bottom part is also on a horizontal plane. The horizontal planes of the first opening of the top cover and the second opening of the bottom part are parallel. The first opening and the second opening are not in contact.

In an embodiment, the intake port and the exhaust port are on the same plane, the plane is in a parallel relationship with the horizontal planes of the end surface of the first opening of the top cover and the end surface of the second opening of the bottom part.

In an embodiment, the middle layer has a stopping element with at least part of a perimeter of an outer edge not smaller than a perimeter of an inner edge of the second opening of the bottom part, which is used to prevent the middle layer from descending.

In an embodiment, a heating plate is flush with a lowest point of the bottom part. In another embodiment, a liquid storage container is provided. The liquid storage container is to moisten pressurized breathable gas delivered to airways. When the liquid storage container and an airflow generator are in an operational position, the liquid storage container can supply heat to liquid within a chamber, and the liquid storage container includes: the bottom part including a second opening that fits with the top cover, at least one receiving part at a front end of the bottom part for engaging with the top cover, and at least one receiving part at a rear end of the bottom part to connect to the top cover. The bottom part includes an integrally formed wall and a heating plate.

The heating plate is configured to conduct heat, integrally formed with the wall of the bottom part, together forming a chamber for containing liquid, with a minimum capacity of the chamber being 150 mL.

The wall of the bottom part has a clamping wall at the connection with the heating plate. The heating plate is embedded into the clamping wall, and an area of the heating plate embedded into the wall of the bottom part is not less than 66 $mm^2$.

In an embodiment, the heating plate, through a surface treatment process, obtains edges with curves or achieves a more robust connection with a clamping wall of the liquid storage container, and the surface treatment process includes metal grinding, spraying, spray sandblasting, polishing, or coating.

In an embodiment, a part of the heating plate that is embedded into the clamping wall has at least one height difference structure.

In another embodiment, a liquid storage container is provided. The liquid storage container is to moisten pressurized breathable gas delivered to airways. When the liquid storage container and an airflow generator are in an operational position, the liquid storage container can supply heat to liquid within a chamber, and the liquid storage container includes: a top cover that is configured to engage with a bottom part through a snap-fit connection and to sealably connect to a middle layer, forming a detachable whole. The top cover includes a first opening formed by a continuous wall. The first opening corresponds to a second opening of a bottom part. The continuous wall includes an intake port and an exhaust port configured to be in communication with the airflow generator. Pipes extend from the intake port and the exhaust port respectively. The top cover further includes a fastener and clip extending from the wall at the first opening to secure the bottom part, and a platform that contacts the middle layer, the platform is configured to press against an upper sealing element on a middle layer.

The middle layer is configured to be detachably connectable to the bottom part, and it includes a stopping element with a perimeter of an outer edge not smaller than a perimeter of an inner edge of a second opening of the bottom part, and a sealing element that contacts the top cover and the bottom part. The bottom part includes a second opening that fits with the top cover, at least one receiving part at a front end of the bottom part for engaging with the fastener of the top cover, and at least one receiving part at a rear end of the bottom part to connect to the clip of the top cover, and the bottom part includes an integrally formed wall and a heating plate. The sealing element is divided into the upper sealing element and a lower sealing element. The stopping element is configured to contact an end surface of the second opening of the bottom part to prevent the middle layer from descending. The upper sealing element is configured to contact the platform of the top cover to form a seal with the top cover, while a perimeter of an outer edge of the lower sealing element conforms to an inner wall of the bottom part to create a seal.

The bottom part includes a second opening that fits with the top cover, at least one receiving part at a front end of the bottom part for engaging with the fastener of the top cover, and at least one receiving part at a rear end of the bottom part to connect to the clip of the top cover, and the bottom part includes an integrally formed wall and a heating plate.

In an embodiment, an end surface of the first opening of the top cover is on a horizontal plane, and an end surface of the second opening of the bottom part is on a horizontal plane. The horizontal planes where the first opening of the top cover and the second opening of the bottom part coincide. The first opening and the second opening are in contact.

In an embodiment, the middle layer has a stopping element with at least part of a perimeter of an outer edge not smaller than a perimeter of an inner edge of the second opening of the bottom part to prevent the middle layer from descending.

In an embodiment, the upper sealing element and the lower sealing element achieve different degrees of deformation through a design of their wall thicknesses and structures.

In another embodiment, a liquid storage container is provided. The liquid storage container is to moisten pressurized breathable gas delivered to airways. When the liquid storage container and an airflow generator are in an operational position, the liquid storage container can supply heat to liquid within a chamber, and the liquid storage container includes: a top cover which includes a first opening formed by a continuous wall. The first opening corresponds to a second opening of a bottom part. The continuous wall includes an intake port and an exhaust port configured to be in communication with the airflow generator. Pipes extend from the intake port and the exhaust port respectively. The top cover further includes a fastener and clip extending from the wall at the first opening to secure the bottom part, and a platform that contacts the middle layer. At least one fastener is located at a front end of the top cover, and at least one clip is located at a rear end of the top cover. The clip is configured to be at an angle with the wall at the rear end of the top cover.

A middle layer that is configured to be detachably connectable to the bottom part, and seals the top cover and the bottom part.

The bottom part includes a second opening that fits with the top cover, at least one receiving part at a front end of the bottom part for engaging with the fastener of the top cover, and at least one receiving part at a rear end of the bottom part to connect to the clip of the top cover. The bottom part further includes an integrally formed wall and a heating plate.

After connecting the top cover to the bottom part, there is a gap formed between the platform and the end surface of the second opening of the bottom part to accommodate the sealing element on the middle layer. The gap is smaller than the height of the upper sealing element.

In an embodiment, the bottom part includes at least one fixing section configured to increase the friction between the liquid storage container and the airflow generator, and the fixing section of the bottom part has a form of small protrusions of the same material or different materials.

In an embodiment, an end surface of the first opening of the top cover is on a horizontal plane, and an end surface of the second opening of the bottom part is also on a horizontal plane. The horizontal planes of the first opening of the top cover and the second opening of the bottom part coincide. The first opening and the second opening are in contact.

In an embodiment, the middle layer has a stopping element with at least part of a perimeter of an outer edge not smaller than a perimeter of an inner edge of the second opening of the bottom part, which is used to prevent the middle layer from descending.

In another embodiment, the bottom part also includes corresponding steps, configured to guide the liquid storage container into the airflow generator.

In another embodiment, a liquid storage container is provided. The liquid storage container is to moisten pressurized breathable gas delivered to airways. When the liquid storage container and an airflow generator are in an operational position, the liquid storage container can supply heat to liquid within a chamber, and the liquid storage container includes: a bottom part including a second opening that fits with a top cover, at least one receiving part at a front end of the bottom part for engaging with the top cover, and at least one receiving part at a rear end of the bottom part to connect to the top cover, and the bottom part includes an integrally formed wall and a heating plate.

The heating plate is configured to conduct heat, integrally formed with the wall of the bottom part, together forming a chamber for containing liquid.

The wall of the bottom part has a clamping wall at the connection with the heating plate. The heating plate is embedded into the clamping wall, and an embedded part of the heating plate has at least one height difference structure of not less than 0.3 mm, which is used to prevent liquid inside the chamber from leaking to an exterior of the chamber.

In an embodiment, the heating plate, through a surface treatment process, obtains edges with curves or achieves a more robust connection with the clamping wall of the liquid storage container, and the surface treatment process includes metal grinding, spraying, spray sandblasting, polishing, or coating.

In an embodiment, the height difference structure has an arc shape.

Implementing the liquid storage container in the disclosure provides at least the following beneficial effects:

1. The separable structure on a flat plane is easier to install and use: Most liquid storage containers on the market have their top cover and bottom part connected by hinges. The advantage of hinge connections is that they can ensure the integration of the liquid storage container, thus preventing the loss of parts. Hinge connections can be categorized into non-detachable and detachable types. a. Non-detachable hinge connections, while ensuring the integration of the liquid storage container, have the situation of an unreasonable hinge design. The top cover of the liquid storage container cannot be completely laid flat and can only hang in the air via the hinge, which can lead to uneven force distribution and flip the liquid storage container over, or cause it to close while it is filling with water. The former may result in the spilling of water from the liquid storage container, and the latter may lead the patient's fingers to get pinched. b. The removable hinge, due to its mechanical structure, cannot be easily detached and there is a risk of damage at the hinge of the top cover during the disassembly process: due to structural requirements of the hinge, there are certain gaps at the connection area, which can easily accumulate dirt and are difficult to clean. The sealing element within the liquid storage container requires contact and compression with the platform of the upper and lower covers of the liquid storage container to form a seal, and the platform area must be sufficient to achieve a good seal. Most liquid storage containers on the market have the platform of the lower cover directly at the opening of the lower cover, which, during production, blocks the direct output of the product, thereby increasing production costs. The connection structure of the top cover and bottom part inside the liquid storage container is designed as a simple removable connection, and the connection between the sealing element and the platform is redesigned. The liquid storage container is divided into three parts: the top cover, the middle layer, and the bottom part. This simplifies the complex structure of the components, allowing the three parts to be more easily demolded in production without the obstruction of platforms or protrusions. The components are connected through simple mechanical means: a. The connection between the top cover and the bottom part is made using a protruding snap-fit form connection, which avoids the issue of non-removable hinges: b. The middle layer includes a sealing element and a stopping element, both produced by an integrated molding process. The stopping element of the middle layer comes into direct contact with the open end surface of the bottom part, forming a platform that limits the movement of the sealing element. The connection areas of the three components are all configured to be flat and, through a simple connection design, solving the following problems: a. The difficulties of the liquid storage container's lower cover in production are solved: b. It allows for a simple connection or disassembly of the top covers and lower covers. c. Installing the middle layer directly on the bottom part with a flat surface is easier to operate, compared to installing the sealing element on the top cover that is fixed by hinges, improving user-friendliness: d. The open end surface of the bottom part being flat, as opposed to non-flat, makes patients less prone to misjudge the water level. e. The connection between the top cover and the bottom part being fully detachable does not hinder the patient from adding water due to the presence of the top cover.

2. The structural design of the middle layer: In ordinary liquid storage containers, the seal is fixedly connected to the top cover, and then comes into contact with the platform of the bottom part form a seal. This connection method requires the patient to ensure that the top cover and the seal are tightly connected: otherwise, it is very likely that the sealing element will fall off when the top cover connects to the bottom part. Some liquid storage containers are manufactured with sealing elements using an integrally formed method. This type of connection usually makes the sealing elements difficult to replace and results in high maintenance or replacement costs. The choice of sealing material also needs to be based on the characteristics of the liquid storage container material, which narrows the range of options. Combining the platform that restricts the sealing element with the ordinary sealing element not only optimizes the production of the components but also provides double assurance for the gas and liquid seals of the entire liquid storage container. The middle layer includes a stopping element, an upper sealing element, and a lower sealing element. The stopping element has at least a part of its perimeter of the outer edge that is not smaller than a perimeter of an inner edge of the second opening of the bottom part, which is used to prevent the middle layer from descending. The upper seal includes support arms of a certain height and extended thin sheets. There is a certain gap between the thin sheets and the stopping element to facilitate the deformation of the upper sealing element when it contacts the platform of the top cover. The perimeter of the outer edge of the lower sealing element is slightly larger than the perimeter of the inner edge of the wall of the bottom part of the liquid storage container. It can rely on its own material characteristics to deform during connection, sealing the opening of the bottom part, and forming a tight anti-overflow ring.

3. The heating plate and the bottom part are integrally formed and connected to the wall. Heating plates are commonly connected to the wall of the bottom part with materials such as silicone or rubber. However, materials like silicone and rubber are prone to deformation and aging due to continuous exposure to high temperatures, which can consequently reduce the sealing ability of the liquid storage container. Therefore, the heating plate is integrally formed with the wall of the bottom part of the liquid storage container through a molding connection, which can effectively reduce the separated seams or connection points, provide higher structural strength and stability, reduce the risk of leakage, and due to the reduction of excess processes, improve production and inspection efficiency, save time and labor costs, and reduce the defect rate of the products.

4. Environmentally Friendly: Combining the above three points, the redesign of the liquid storage container significantly reduces unnecessary waste of resources, both in terms of production, manufacturing, and material selection. This makes the overall production process simpler and uses fewer materials while still ensuring air-tightness. The conservation of resources during the production process helps to reduce the emission of greenhouse gases, thereby alleviating the pressure of climate change, reducing the exploitation of natural resources, and lessening the damage to the natural environment, establishing a healthier and more sustainable future.

DETAILED DESCRIPTION

To make the objectives, features, and advantages of this disclosure more apparent and understandable, the specific embodiments of the disclosure are described in detail in conjunction with the accompanying drawings. Many specific details are set forth in the following description to provide a thorough understanding of the disclosure. However, this disclosure can be implemented in many other ways different from those described here, and those skilled in the art can make similar improvements without violating the essence of the disclosure. Therefore, this disclosure is not limited by the specific embodiments disclosed below.

Unless otherwise defined, all technical and scientific terms used in this document have the same meaning as commonly understood by those skilled in the art of this disclosure. The terms used in the description of the disclosure herein are for the purpose of describing particular embodiments only and are not intended to limit the disclosure.

Figure 24A:
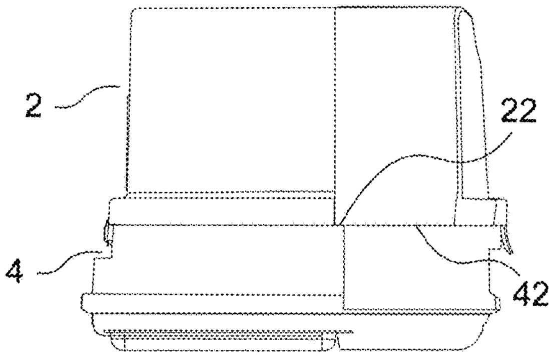
FIGS. 24A and 24B are schematic diagrams where the first opening of the top cover and the second opening of the bottom part are on different planes in accordance with an embodiment.
Figure 24B:
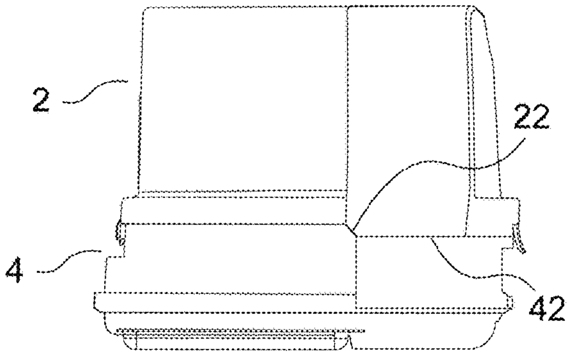

This disclosure divides the liquid storage container 1 into three parts: the top cover 2, the middle layer 3, and the bottom part 4. As shown in FIG. 24A, the end surface of the first opening 22 of the top cover 2 is on the same horizontal plane in some embodiments, and the end surface of the second opening 42 of the bottom part 4 is also on the same horizontal plane in some embodiments. In this case, the horizontal planes of the first opening 22 of the top cover 2 and the second opening 42 of the bottom part 4 can coincide or be parallel, and the first opening 22 and the second opening 42 can be in contact or not in contact. As shown in FIG. 24B, the end surface of the first opening 22 of the top cover 2 is on different horizontal planes in some embodiments, being a stepped plane, and the end surface of the second opening 42 of the bottom part 4 is also on different horizontal planes in some embodiments, being a stepped plane. The connection structure of the top cover 2 and the bottom part 4 is configured to be a simple and fully detachable connection, which can be a snap-fit connection, magnetic attraction connection, push-pull buckle, etc. The middle layer directly contacts and connects with the bottom part 4 to form the basis for sealing the bottom part 4, and then is joined with the top cover 2. The platform 27 of the top cover 2 compresses the middle layer 3 to achieve an overall sealed state.

The following describes several structures of the liquid storage container of the disclosure, in conjunction with specific embodiments.

Embodiment 1

Figure 1:
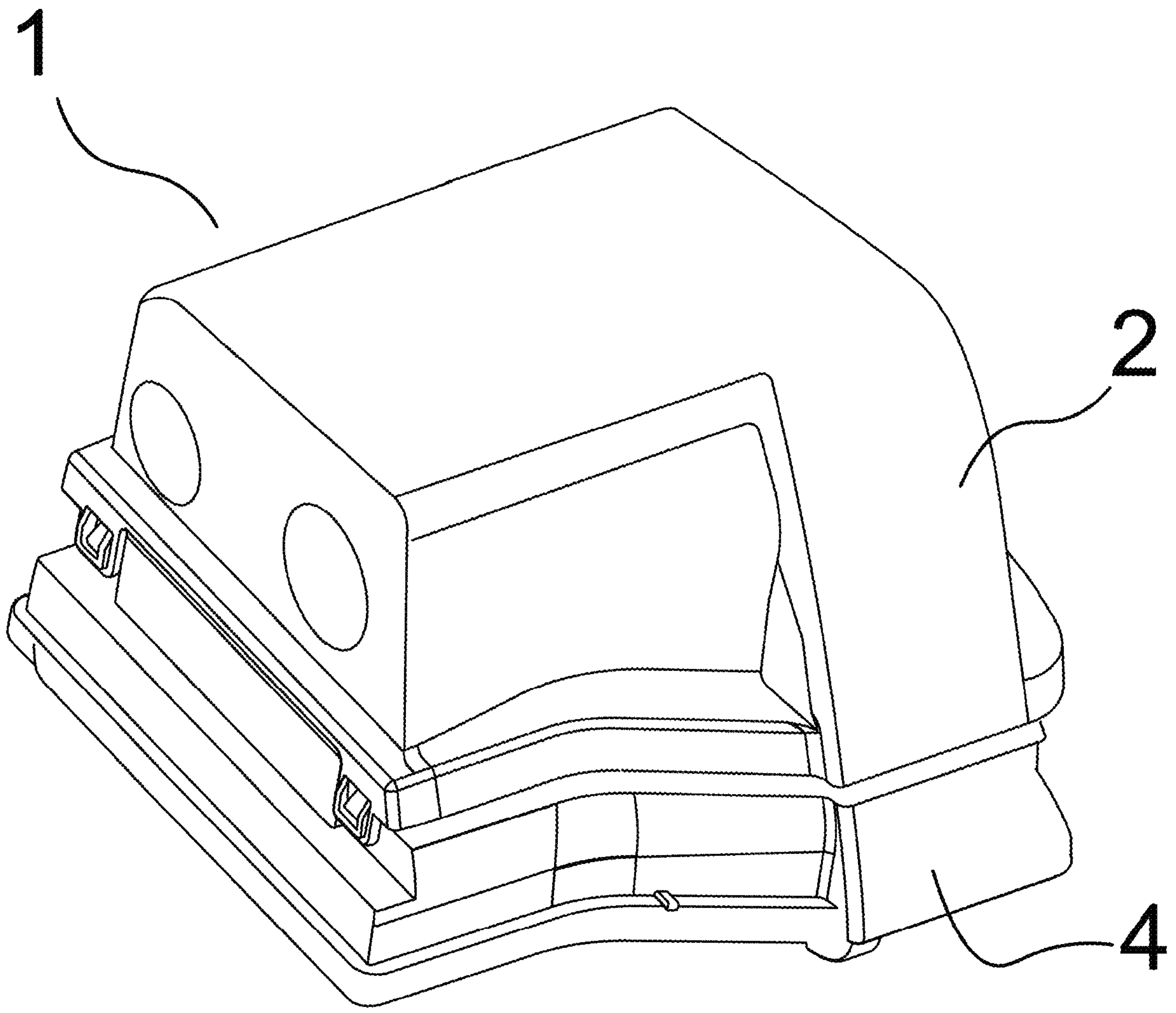
FIG. 1 is a schematic diagram of the structure of a liquid storage container in accordance with an embodiment.
Figure 2:
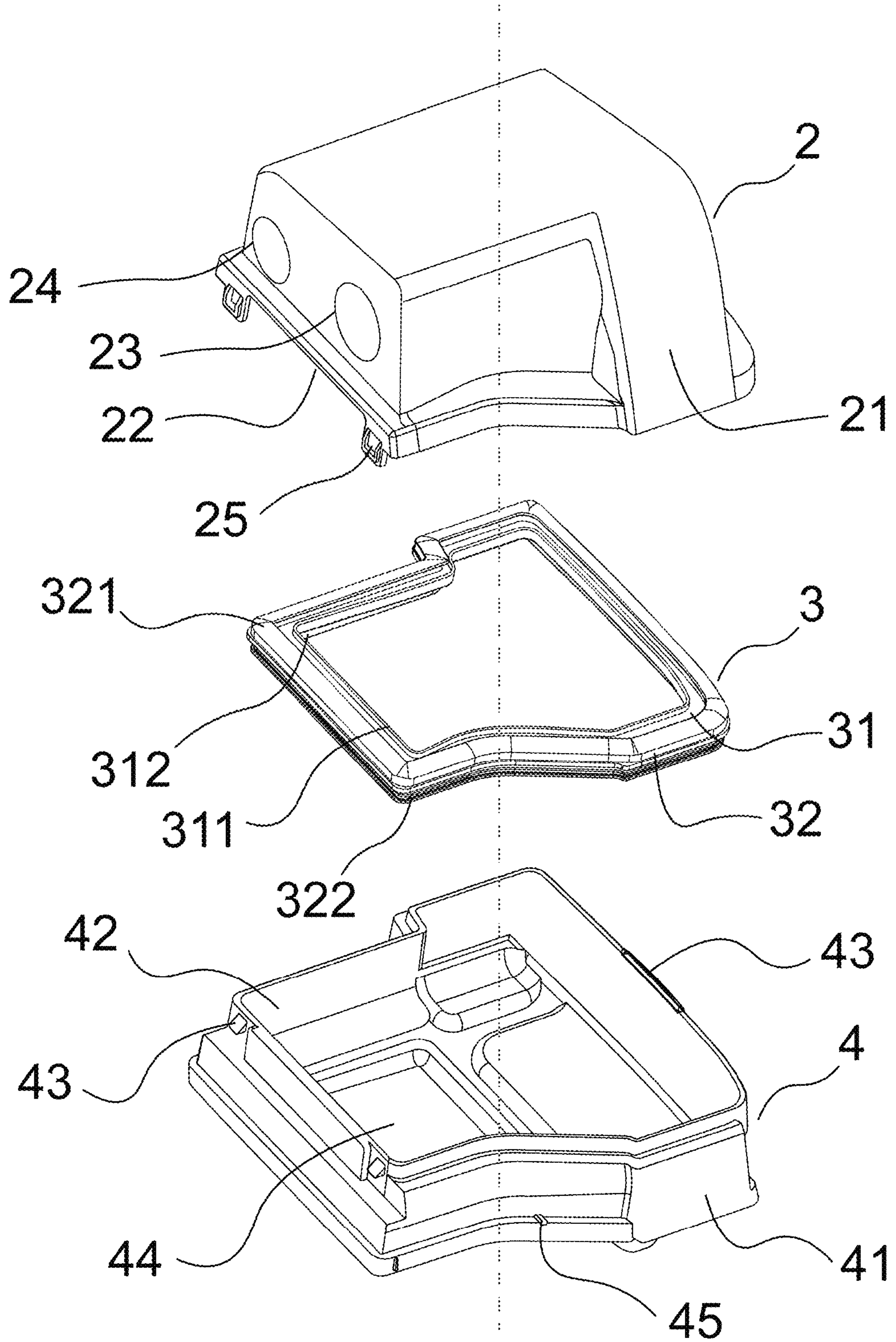
FIG. 2 is an exploded schematic diagram of the structure of a liquid storage container in accordance with an embodiment.
Figure 3:
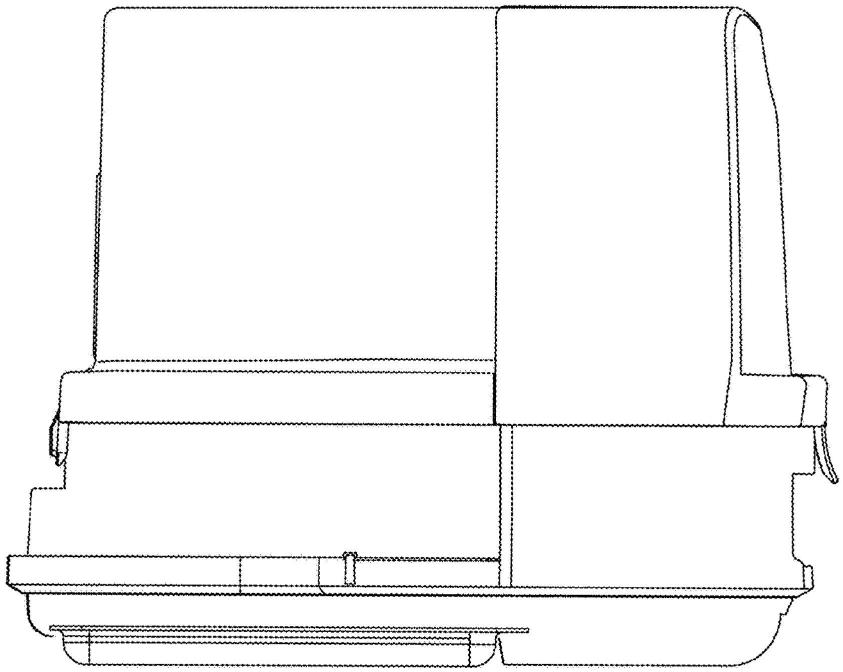
FIG. 3 is a schematic diagram of the zoning of a liquid storage container in accordance with an embodiment.
Figure 4:
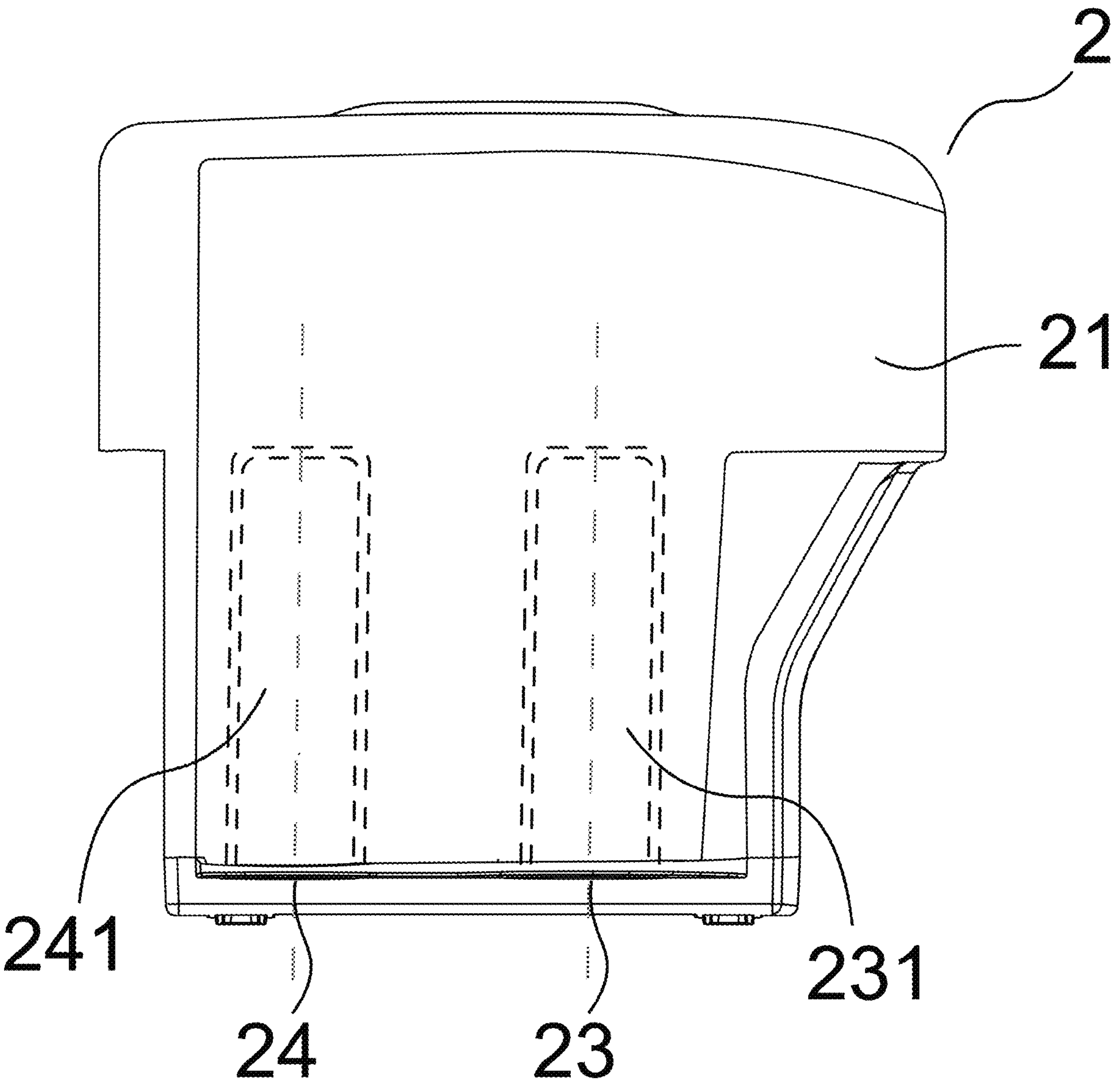
FIG. 4 is a top view of the top cover of a liquid storage container in accordance with an embodiment.
Figure 5:
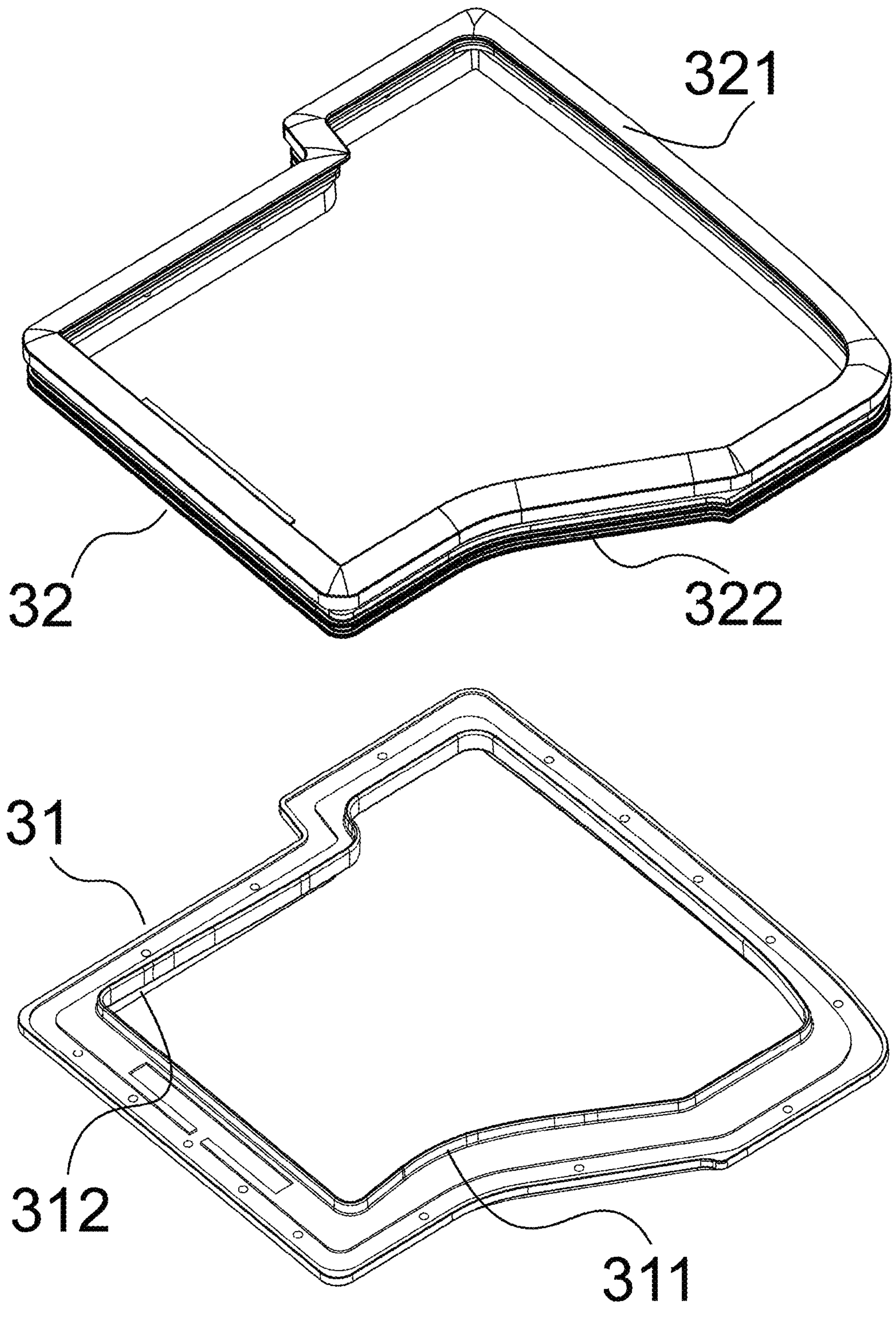
FIG. 5 is an exploded schematic diagram of the structure of the middle layer of a liquid storage container in accordance with an embodiment.
Figure 6:
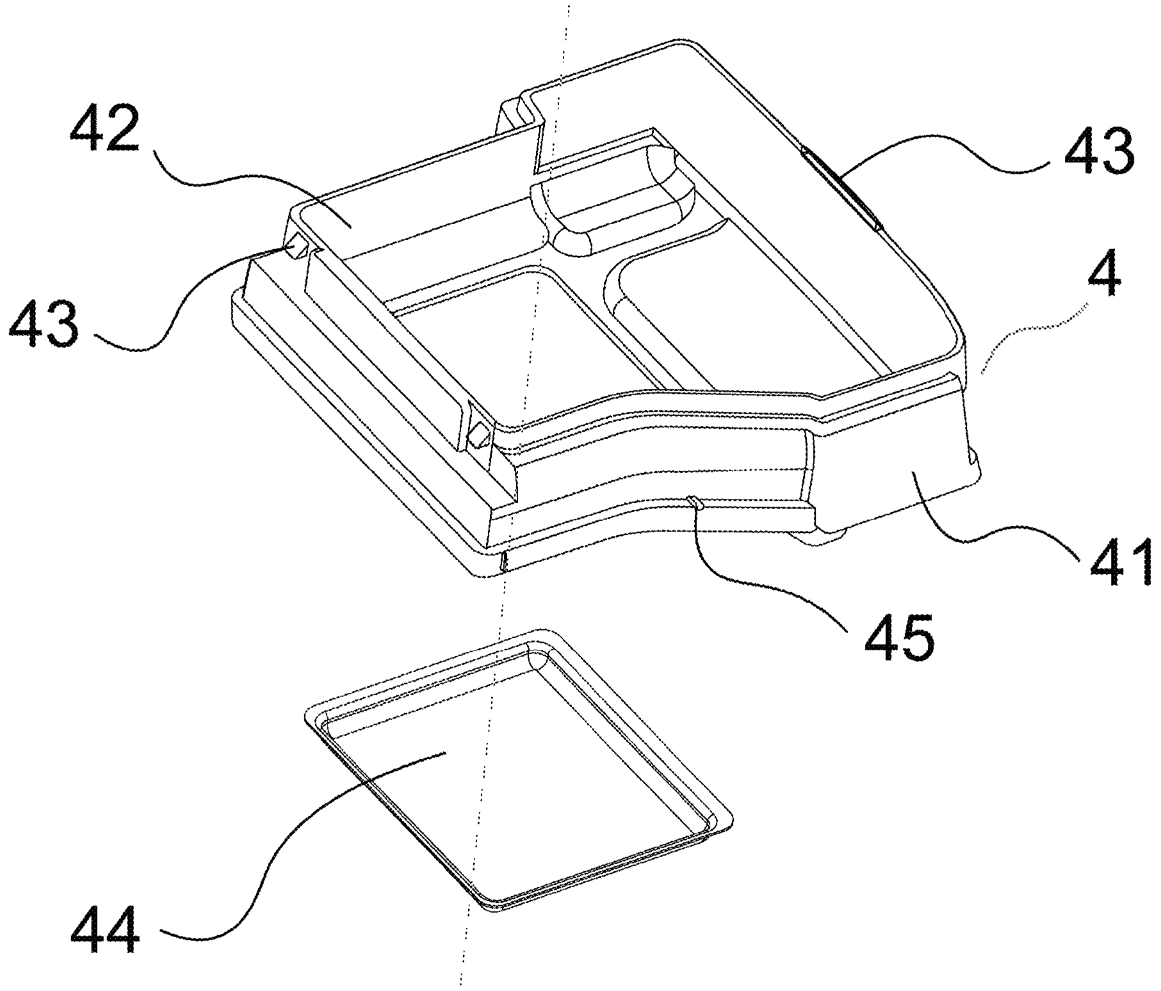
FIG. 6 is an exploded schematic diagram of the structure of the bottom part of a liquid storage container in accordance with an embodiment.
Figure 28:
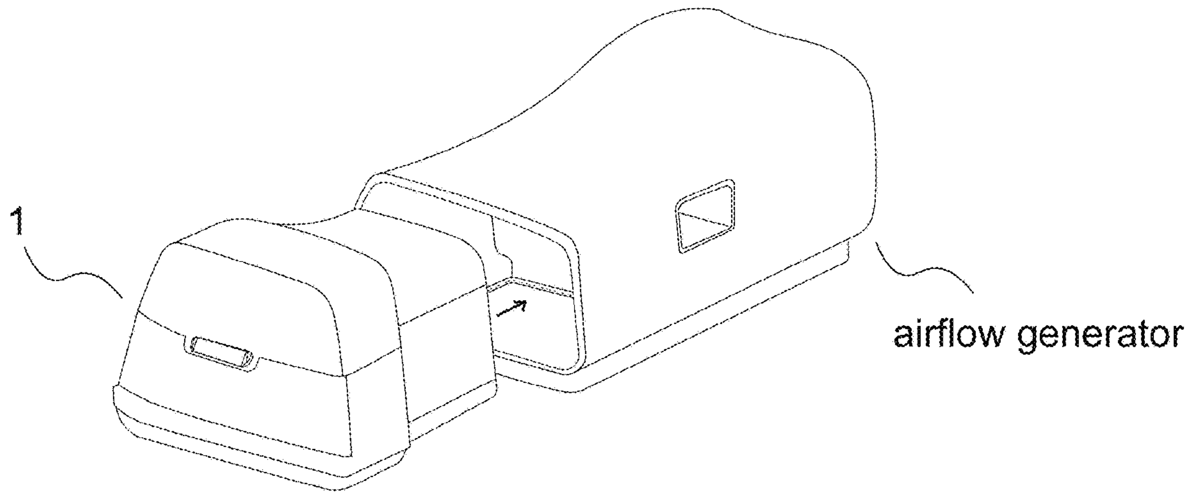
FIG. 28 is a three-dimensional schematic diagram of the liquid storage container and airflow generator.
Figure 29A:
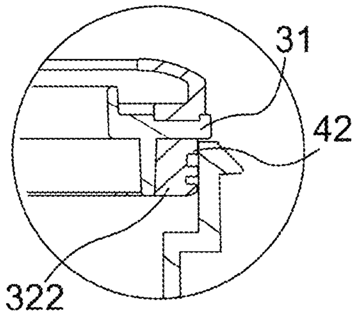
FIGS. 29A, 29B, 29C, 29D and 29E are schematic diagrams showing different forms of the upper sealing element and the lower sealing element.
Figure 29B:
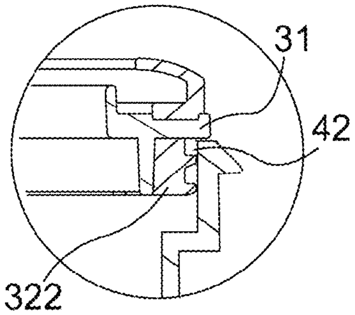
Figure 29C:
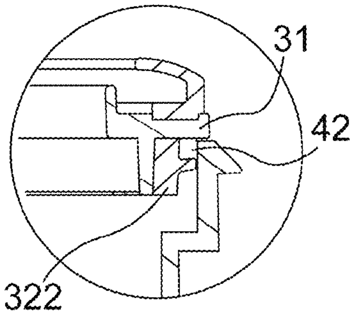
Figure 29D:
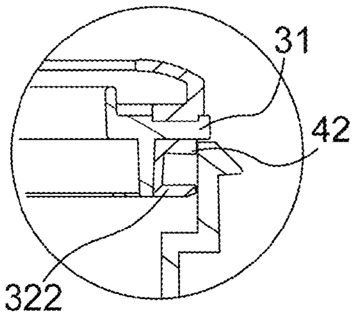
Figure 29E:
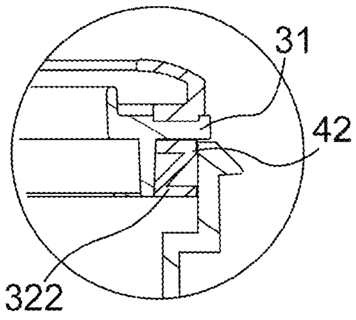

In this embodiment, a liquid storage container 1, used to moisten pressurized breathable gas delivered to a patient, can provide heat to the liquid stored within the chamber when connected to an airflow generator in a working position (as shown in FIG. 28). The liquid storage container 1 includes a top cover 2, a middle layer 3, and a bottom part 4. As shown in FIG. 3, the liquid storage container 1 is divided into a front end and a rear end, with the top cover 2, the middle layer 3, and the bottom part 4 each having corresponding front and rear ends.

Figure 7A:
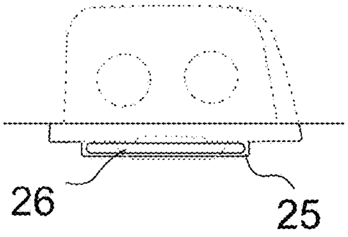
FIGS. 7A, 7B and 7C are schematic diagrams of the forms of the fastener of the top cover of a liquid storage container in accordance with an embodiment.
Figure 7B:
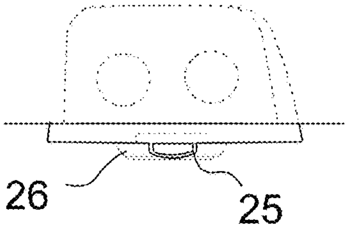
Figure 7C:
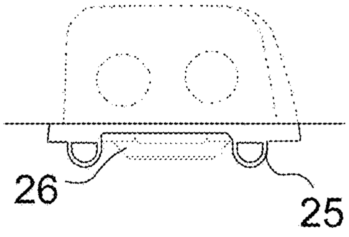
Figure 8:
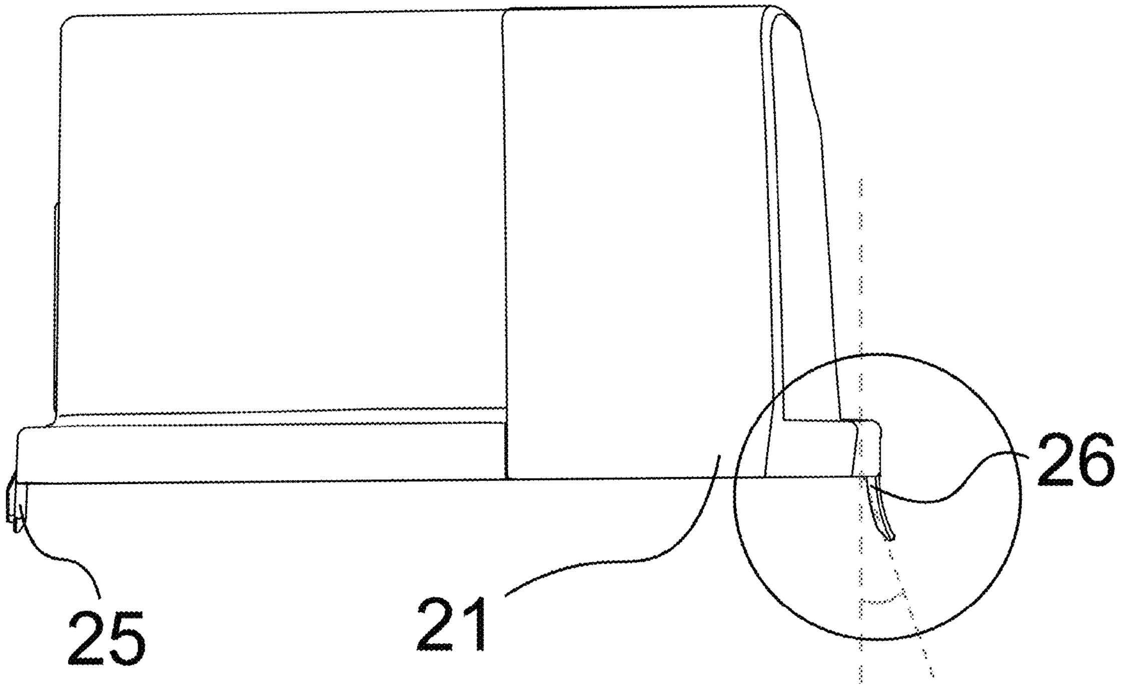
FIG. 8 is a schematic diagram of the angle of the clip on the top cover of a liquid storage container in accordance with an embodiment.
Figure 9A:
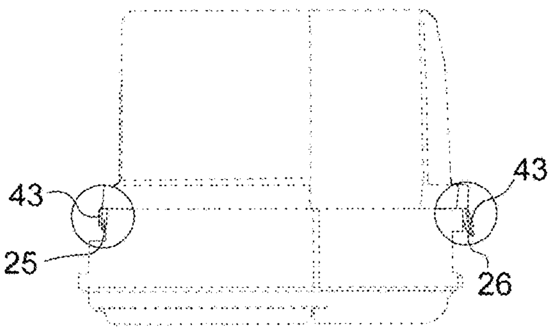
FIGS. 9A, 9B, 9C and 9D are schematic diagrams of the connection forms between the top cover and the bottom part of a liquid storage container in accordance with an embodiment.
Figure 9B:
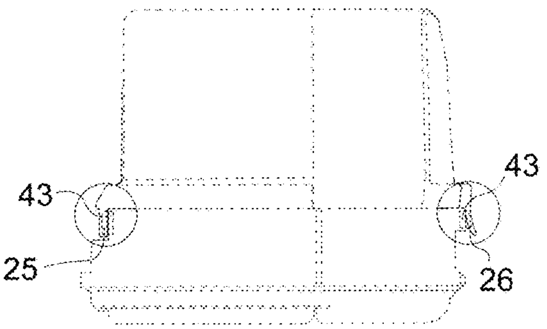
Figure 9C:
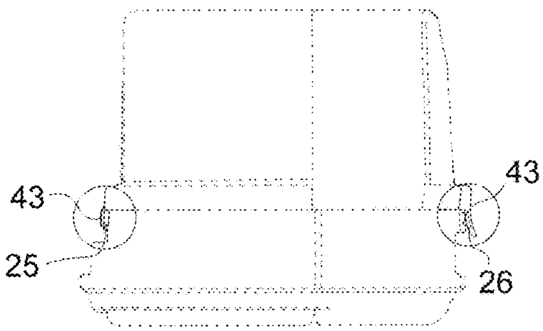
Figure 9D:
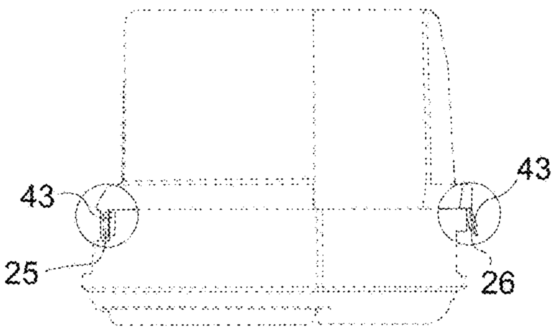
Figure 10A:
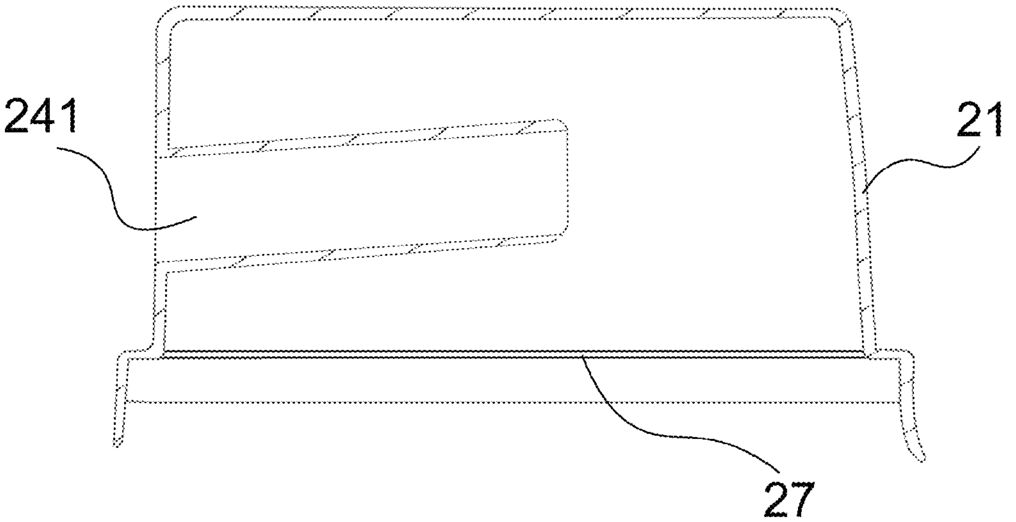
FIGS. 10A and 10B are schematic diagrams of the position of the platform of the top cover of a liquid storage container in accordance with an embodiment.
Figure 10B:
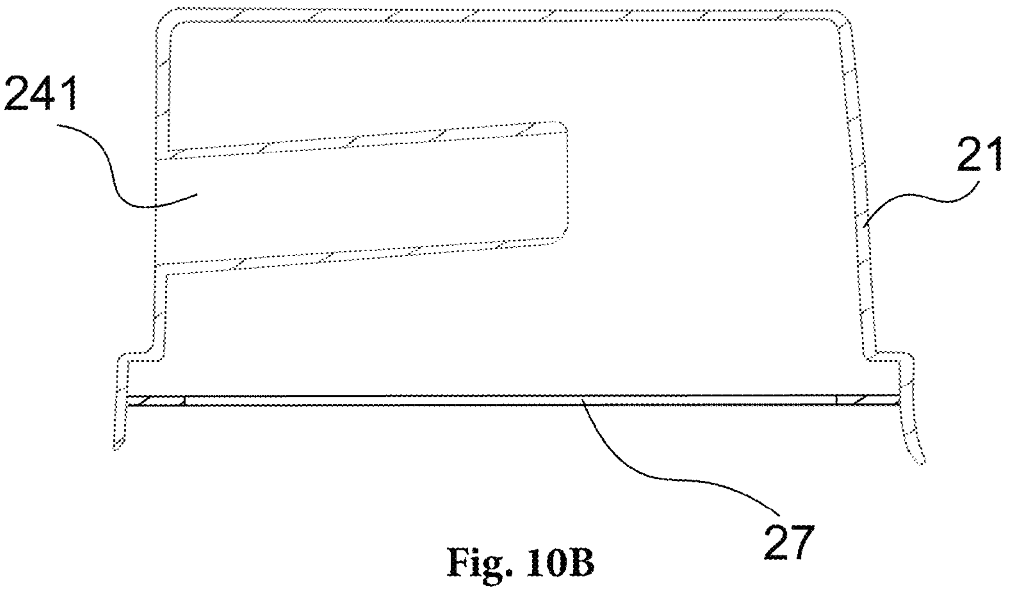
Figure 11A:
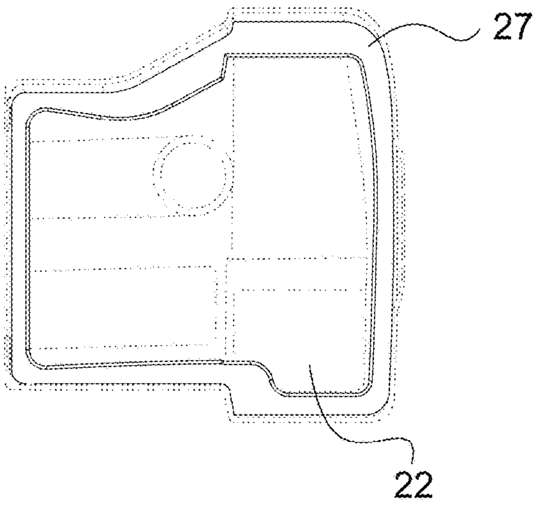
FIGS. 11A and 11B are schematic diagrams of different forms of the platform of the top cover of a liquid storage container in accordance with an embodiment.
Figure 11B:
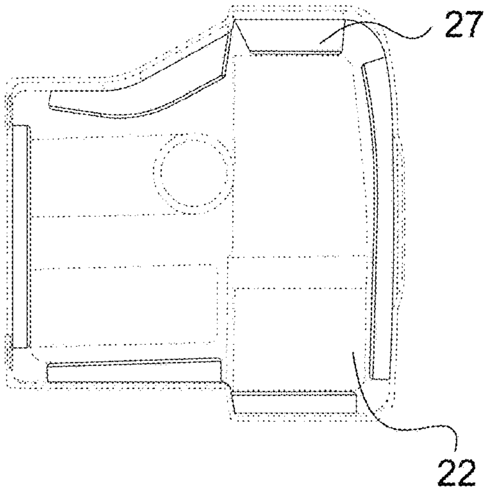
Figures 12A, 12B, 12C:
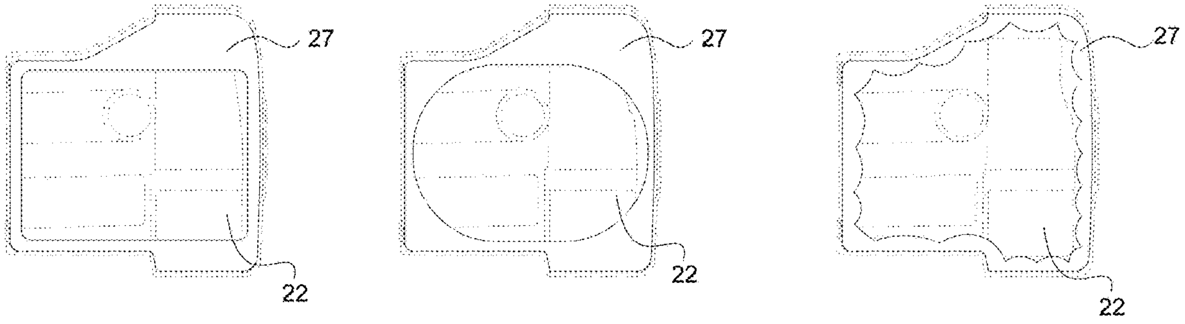
FIGS. 12A, 12B and 12C are schematic diagrams of different forms of the platform of the top cover of a liquid storage container in accordance with an embodiment.
Figures 14A, 14B:
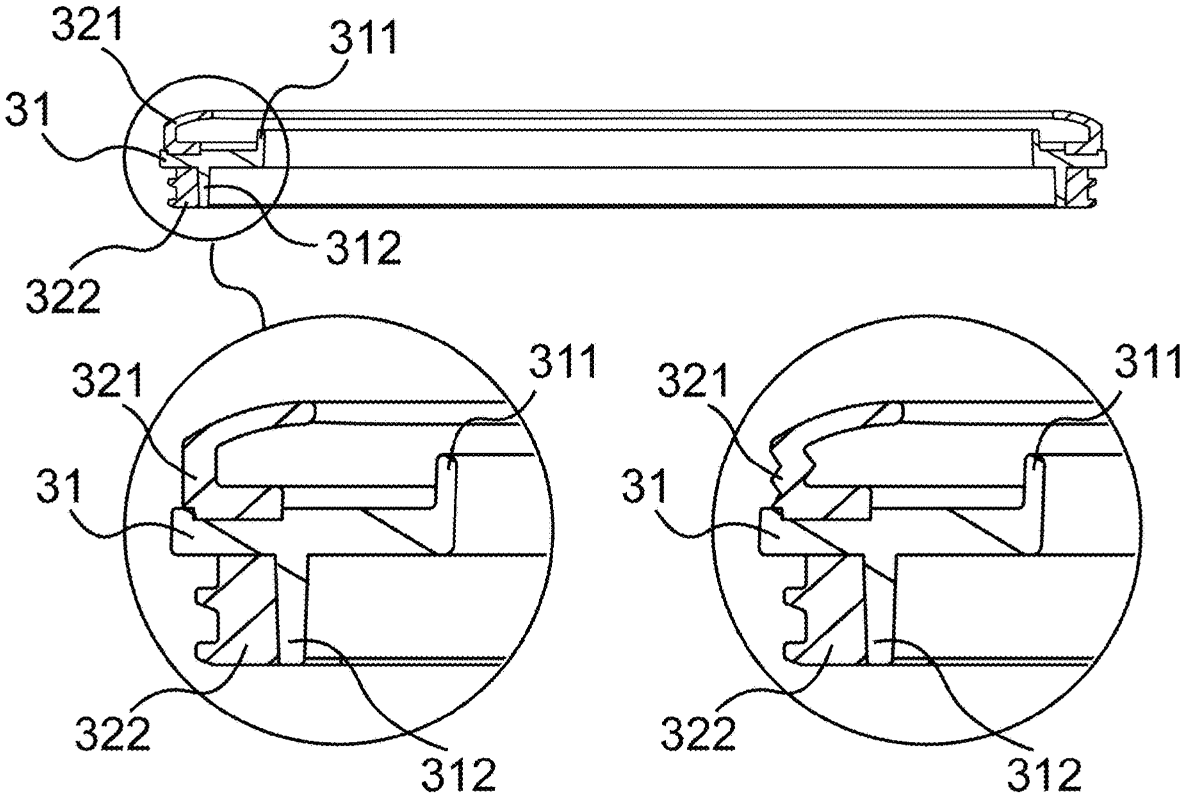
FIGS. 14A and 14B are schematic diagrams of the structure of the sealing element of the middle layer of a liquid storage container in accordance with an embodiment.
Figure 15:
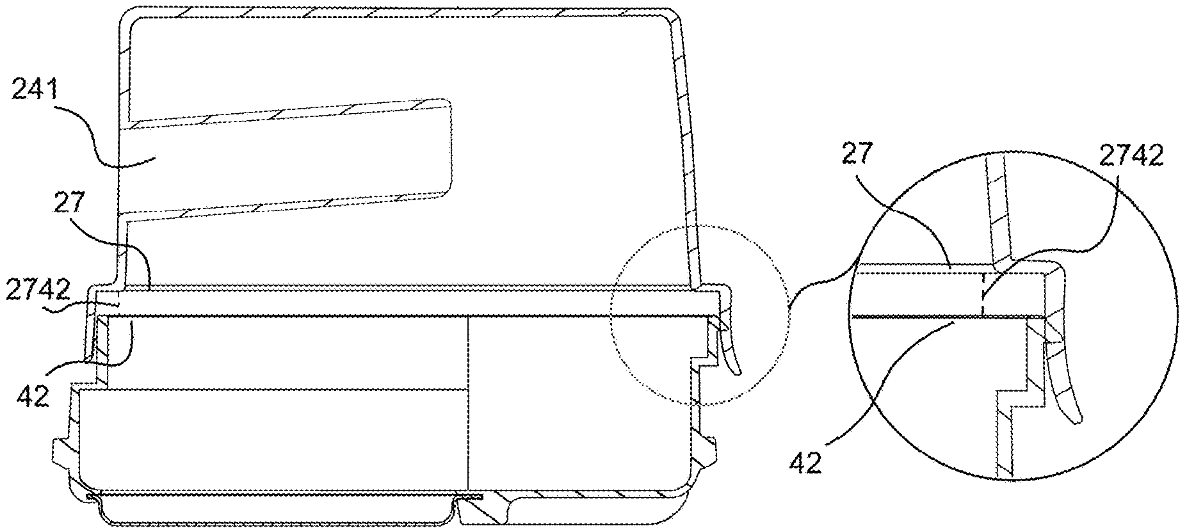
FIG. 15 is a schematic diagram of the gap formed when the platform of the top cover and the bottom part are connected in a liquid storage container in accordance with an embodiment.
Figure 16:
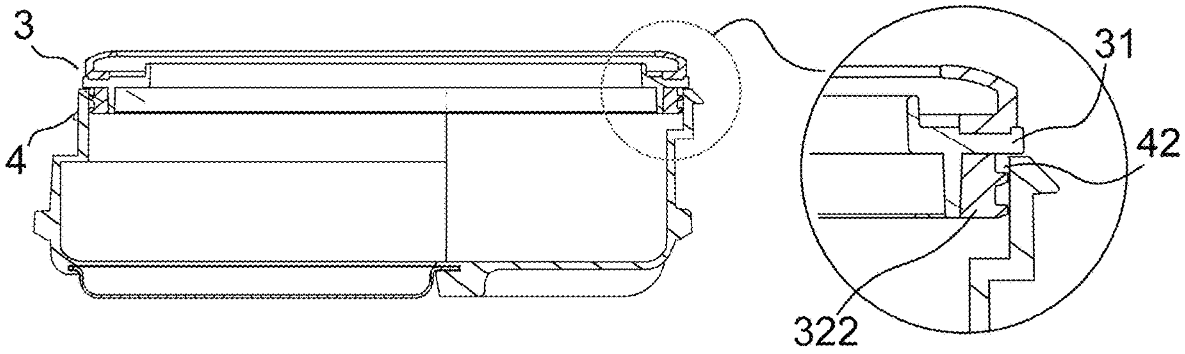
FIG. 16 is a schematic diagram of the structure of the connection between the stopping element of the middle layer and the bottom part of a liquid storage container in accordance with an embodiment.

The top cover 2 is configured to connect to the bottom part 4 and to seal, contact and connect to the middle layer 3 to form a detachable whole. Specifically, as shown in FIGS. 1 to 18, the top cover 2 includes a first opening 22 formed by a continuous wall 21 and the first opening 22 which corresponds to the bottom part 4. The continuous wall 21 includes an intake port 23 and an exhaust port 24 configured to be in communication with the airflow generator, and the pipe 231 and pipe 241 which extend from the intake port 23 and the exhaust port 24 (pipe 231 extends from the intake port 23 and pipe 241 extends from the exhaust port 24). Extending from the wall 21 at the first opening 22 are a fastener 25 and a clip 26 that secure the bottom part, and a platform 27 that contacts the middle layer 3. The continuous wall 21 of the top cover 2 can be smoothly formed or bent and connected, and its external wall contour can be configured according to the position provided by the airflow generator. The wall 21 is at least partly rigid and can be made from one or more materials such as polyethylene, polypropylene, polycarbonate, silicone, rubber, thermoplastic elastomers, etc. Protrusions or grooves can be set on the wall 21 to increase friction, facilitating patient grip or creating a tighter connection with the airflow generator. The end surface of the first opening 22 formed by the wall 21 is on a horizontal plane (in other words, the end surface of the first opening is a flat surface), and the edges connecting the top cover 2 and the bottom part 4 are aligned: the perimeter of the inner edge of the first opening 22 of the top cover 2 is greater than or equal to the perimeter of the outer edge of the sealing element 32 of the middle layer 3. The intake port 23 and exhaust port 24 on the wall 21 are on the same plane, which can be perpendicular to the horizontal plane, at a certain angle to the horizontal plane, or parallel to the horizontal plane. The contours of the intake port 23 and the exhaust port 24 can be circular, oval, semicircular, or square. The pipe 231 and pipe 241 that are extending from the intake port 23 and exhaust port 24 are parallel to each other, and the intake port 23 includes a first section 2411 and a second section 2412, and the first section 2411 and the second section 2412 are not parallel. The second section 2412 extends towards the bottom part 4 and is perpendicular to the horizontal plane (perpendicular to the coronal plane and sagittal plane). The second section 2412, with its shorter length compared to the first section 2411, ensures that it does not contact or is not in proximity to the water surface, preventing the splashing of water. The pipe 231 and pipe 241 that are extending from the intake port 23 and the exhaust port 24 are made from the same material as the rigid part of wall 21 of the top cover 2. Extending from the front end of the first opening 22 is at least one fastener 25 that is fixed to the bottom part 4. The fastener 25 can match and connect to the receiving part 43 of the bottom part 4. As shown in FIGS. 9A, 9B, 9C and 9D, the connection can be a snap-fitting, magnetic attraction, etc., securing the front end of the top cover 2 and the front end of the bottom part 4. FIG. 9A shows a snap-fit connection form, FIG. 9B shows a magnetic attraction form, and FIGS. 9C and 9D show a combination of snap-fit and magnetic attraction: as shown in FIG. 7, the external contour of fastener 25 can be square, U-shaped, or other shapes that facilitate easy snapping, and fastener 25 has a beveled surface to ease the snapping of the top cover 2 with the bottom part 4. The fastener 25 can be made from materials such as polyethylene, polypropylene, polycarbonate, silicone, thermoplastic elastomers, etc. Extending from the rear end of the first opening 22 is at least one clip 26 fixed to the bottom part 4. The clip 26 can be matched and connected to the receiving part 43 of the bottom part 4, securing the rear end of the top cover 2 to the rear end of the bottom part 4. The connection can take the form of a snap-fit, magnetic attraction, etc. As shown in FIG. 8, the extended clip 26 is formed at an angle with the wall 21 at the rear end of the top cover 2. The angle is approximately at or between 0 to 75 degrees, creating a distance between the clip 26 and the bottom part 4, making it convenient for patients to grip with their fingers. The top cover 2 has a platform 27 in contact with the middle layer 3 (the platform does not necessarily refer to steps that are on the same horizontal plane). After connecting the top cover 2 to the bottom part 4, as shown in FIG. 15, there is a gap 2742 formed between the platform 27 and the end surface of the second opening 42 of the bottom part 4 to accommodate the sealing element 32 on the middle layer 3. The gap 2742 is smaller than the height of the upper sealing element 321. As shown in FIGS. 10A and 10B, the platform 27 can be located at the end surface of the first opening 22 (as shown in FIG. 10B) or above the end surface (as shown in FIG. 10A). The platform 27 extends from the wall 21 of the top cover 2, and the maximum distance of the extension does not exceed 15 mm, ensuring easy demolding during production and providing a sufficient contact surface for the middle layer 3 to achieve sealing. As shown in FIGS. 11A and 11B, the platform 27 can have a uniform extension or a non-uniform extension, and it can be continuous or discontinuous. As shown in FIGS. 12A, 12B and 12C, the inner contour shape of the platform 27 can be the contour shape of the top cover 2 on the horizontal plane, square, elliptical, or circular. The platform 27 can be made from materials selected from polyethylene, polypropylene, polycarbonate, silicone, rubber, or others.

Figure 13A:
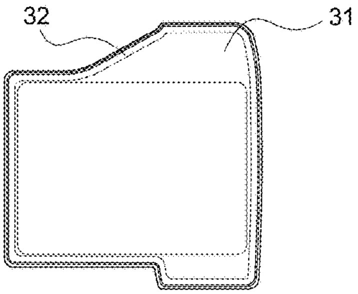
FIGS. 13A, 13B and 13C are schematic diagrams of different forms of the stopping element of the middle layer of a liquid storage container in accordance with an embodiment.
Figure 13B:
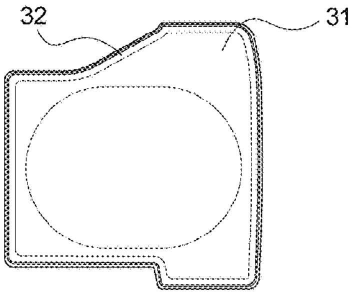
Figure 13C:
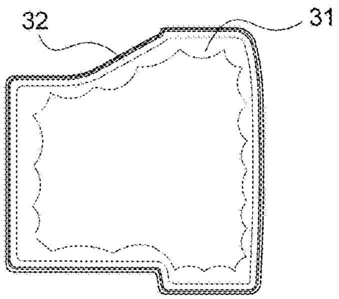

The middle layer 3 is configured to be detachably connectable to the bottom part 4 and it seals the top cover 2 and the bottom part 4. The middle layer 3 includes a stopping element 31 with a perimeter of the outer edge not smaller than a perimeter of an inner edge of the second opening 42 of the bottom part 4. It also includes sealing elements 32 that come into contact with the top cover 2 and the bottom part 4. The stopping element 31 is configured to contact the second opening 42 of an end surface of the bottom part to prevent the middle layer from descending: the perimeter of the outer edge of the stopping element 31 is not smaller than the perimeter of the inner edge of the second opening 42 of the bottom part 4. As shown in FIGS. 13A, 13B and 13C, the contour shape of the stopping element 31, both internally and externally, can be the contour shape of the bottom part 4 on a horizontal plane or be square, elliptical, wavy, and so on. As shown in FIGS. 14A and 14B, the perimeter of the inner edge of the stopping element 31 can have an upward overflow prevention wall 311 to prevent excessive liquid from overflowing within the container. The height of the overflow prevention wall 311 is approximately at or between 1 to 8 mm. The stopping element 31 also has a downward stop wall 312 to prevent the lower sealing element 322 from being compressed inward by the wall 41 of the bottom part 4, which would otherwise prevent the lower sealing element 322 from performing its sealing ability. The stop wall 312 also ensures a more stable connection between the lower sealing element 322 and the stopping element 31. The height of the stop wall 312 is approximately at or between 1 to 15 mm. The thickness of the stopping element 31 is approximately at or between 1 to 15 mm to prevent it from being too thick and increasing the overall weight, making it inconvenient to use. The main body of the stopping element 31 can be made from rigid materials selected from polyethylene, polypropylene, polycarbonate, etc. The overflow prevention wall 311 can be made from flexible materials with good sealing properties, such as silicone, rubber, or made from the same material as the main body of the stopping element 31. The sealing element 32 is divided into an upper sealing element 321 and a lower sealing element 322. The upper sealing element 321 is configured to contact the platform 27 of the top cover 2, creating a seal with the top cover 2. The perimeter of the outer edge of the lower sealing element 322 conforms to the inner wall of the bottom part 4, forming a seal with the bottom part 4. The inner edge of the bottom part 4 connects with the stopping element 31. Specifically, the upper sealing element 321 includes a support arm of certain height and an extended thin sheet. There is a configured gap between the thin sheet and the stopping element 31, which allows the upper sealing element 321 to deform when it contacts the platform 27 of the top cover 2. The perimeter of the outer edge of the lower sealing element 322 is slightly larger than the perimeter of the inner edge of the wall of the bottom part 4 of the liquid storage container 1. The lower sealing element can rely on its material to deform and seal the opening of the bottom part 4 upon connection, forming at least one tight anti-spill ring. The upper sealing element 321 and the lower sealing element 322 can be made from the same material with either the same or different hardness levels, which can be silicone, rubber, thermoplastic elastomers, or other flexible materials with good sealing properties. The overall height of the upper sealing element 321 is at or between 3 to 10 mm, with the thickness of the supporting arm being at or between 0.5 to 5 mm, and the thickness of the thin sheet is at or between 0.3 to 2.5 mm. The total height of the lower sealing element 322 is at or between 3 to 15 mm, with a thickness of at or between 0.5 to 5 mm. Limiting the dimensions is to prevent the flexible material from being too thin or too thick (which could hinder its ability to deform), therefore hindering it from achieving a seal with either the top cover 2 or the bottom part 4. Additionally, the stopping element 31 can include at least one through-hole to allow the sealing element 32 to pass through during manufacturing, thereby forming both the upper sealing element 321 and the lower sealing element 322 at the same time. The upper sealing element 321 and the lower sealing element 322 achieve different degrees of deformation through their wall thickness and structural design (for example, the lower sealing element is set as E-type, F-type, T-type and Z-type, while the upper sealing element is set as C-type, Z-type, as shown in FIGS. 29A, 29B, 29C, 29D and 29E), as shown in FIG. 14. The wall thickness of the lower sealing element 322 is greater than the thin sheet of the upper sealing element 321. There is no gap between it and the stopping element 31. When compressed by the wall 41 of the bottom part 4, it deforms relying on its own material properties. The wall thickness of the upper sealing element 321 sheet is smaller, and there is a certain gap between it and the stopping element 31. When it is compressed by the platform 27 of the top cover 2, it not only deforms itself but is also more easily pressed down, resulting in a greater degree of deformation compared to the lower sealing element 322.

Figure 17:
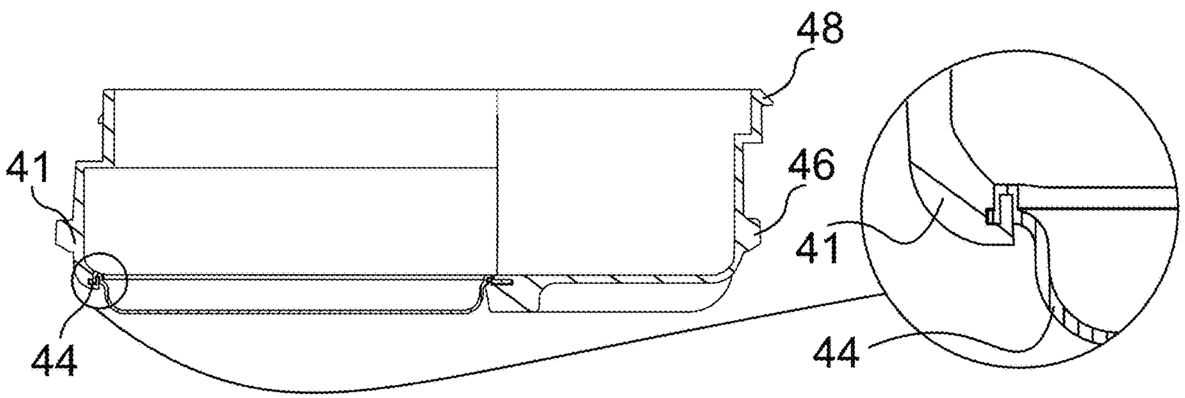
FIG. 17 is a schematic diagram of the structure of the connection between the wall of the bottom part and the heating plate of a liquid storage container in accordance with an embodiment.
Figure 18:
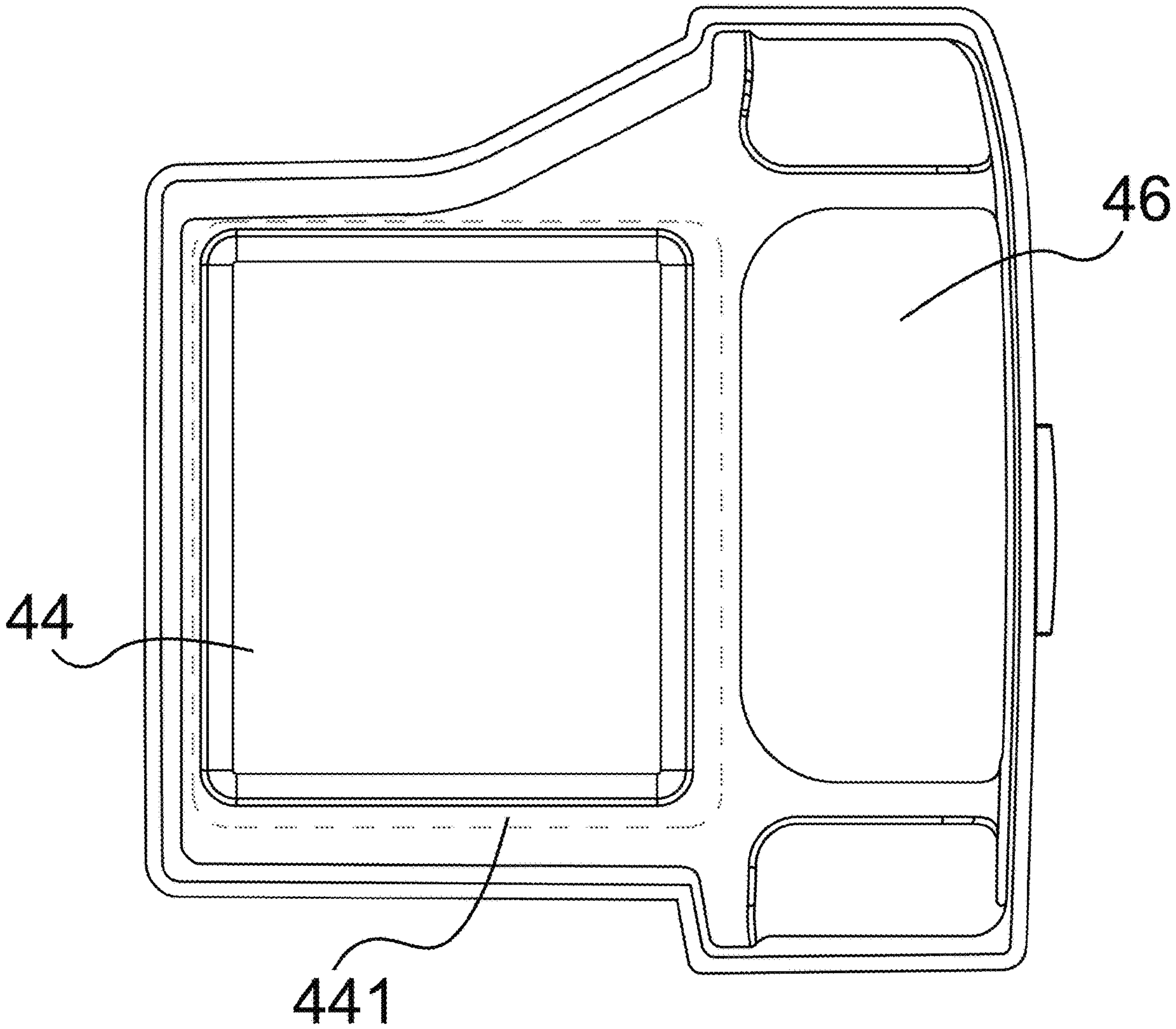
FIG. 18 is a top view of the connection between the wall of the bottom part and the heating plate of a liquid storage container in accordance with an embodiment.
Figure 25:
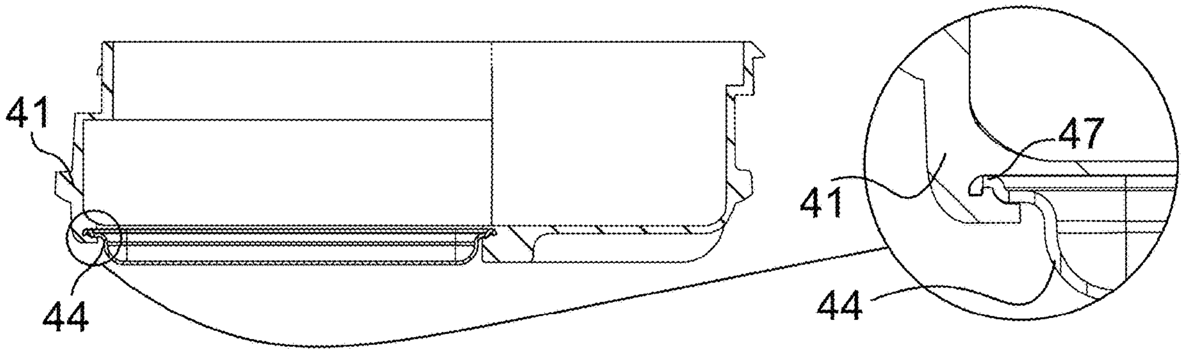
FIG. 25 is a schematic diagram of the structure of the connection between the wall of the bottom part and the heating plate of a liquid storage container in accordance with an embodiment.
Figure 26:
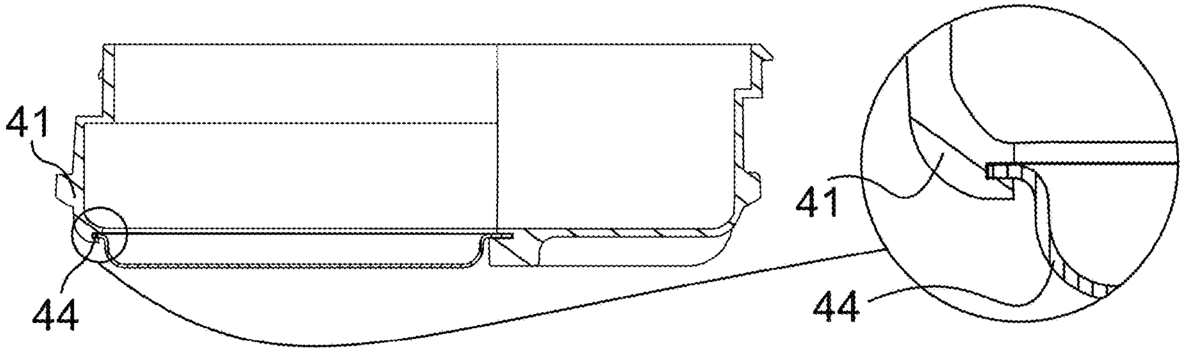
FIG. 26 is a schematic diagram of the structure of the connection between the wall of the bottom part and the heating plate of a liquid storage container in accordance with an embodiment.
Figure 27:
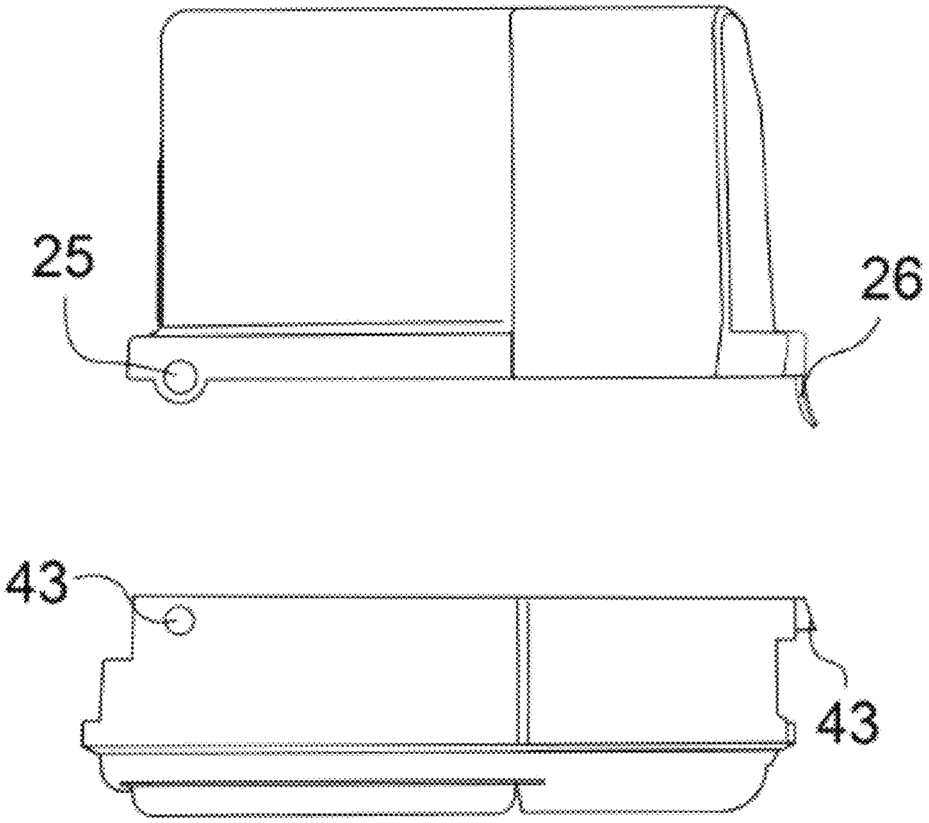
FIG. 27 is a schematic diagram of the connection form between the top cover and the bottom part of a liquid storage container in accordance with an embodiment.

The bottom part 4 includes a second opening 42 that fits with the top cover 2, and at least one receiving part 43 that is situated at the front end of the bottom part 4 to engage with the fastener 25 of the top cover, and at least one receiving part 43 that is positioned at the rear end of the bottom part 4 for connection with the clip 26 of the top cover 2, and an integrally formed wall 41, as well as a heating plate 44 configured to conduct heat. The wall 41 of the bottom part 4 is smooth and integrally formed with the heating plate 44. The external contour of the wall 41 can be configured based on the position (to accommodate the liquid storage container 1) provided by the airflow generator, creating a chamber capable of holding a certain volume of liquid. The minimum capacity of this chamber is 150 mL. Additionally, the rear end of the bottom part 4 includes a section that allows for easy gripping by the patient's fingers. The wall 41 of the bottom part 4 can extend out to form corresponding steps 46 that match and correspond with the airflow generator, configured to guide the liquid storage container 1 into the airflow generator. Additionally, wall 41 features at least one fixing section 45, which serves to increase the friction between the liquid storage container 1 and the airflow generator. The wall 41 of the bottom part 4 is made from a rigid material, which can be polyethylene, polypropylene, polycarbonate, etc. The fixing section 45 can either be a small protrusion made from the same material as the wall 41 of the bottom part 4, or it can be made from flexible materials like silicone, rubber, or thermoplastic elastomers. The end surface of the second opening 42 of the bottom part 4 lies in a horizontal plane (in other words, the end surface of the second opening 42 is a flat surface). The horizontal planes where the end surface of the first opening 22 of the top cover 2 and the end surface of the second opening 42 of the bottom part 4 are located are parallel. The second opening 42 of the bottom part 4 is configured to contact and connect to the stopping element 31 of the middle layer 3, limiting the downward movement of the middle layer 3. As shown in FIG. 27, the receiving parts 43 at the front and rear ends of the bottom part 4 can either be of the same or different designs, which may include protrusions, grooves, magnets, etc. Furthermore, the bottom part 4 may also include at least one locator 48 to facilitate quick and accurate installation of the top cover 2 for patients. The locator 48 can be in the form of protrusions, magnets, etc. As shown in FIGS. 17, 18, 25, and 26, the heating plate 44 is integrally formed and connected with the wall 41 of the bottom part 4. At the connection point between the wall 41 of the bottom part 4 and the heating plate 44, there is a clamping wall 441 (a part of the wall 41 of the bottom part 4). The heating plate 44 is embedded into the clamping wall 441. As shown in FIGS. 17, 25 and 26, there is a gap left between the clamping wall 441 on the outside of the chamber and the heating plate 44. This gap is configured to prevent the wall 41 of the bottom part 4 from squeezing and cracking the heating plate 44 as it cools after production. Additionally, the heating plate 44 undergoes surface treatment processes to acquire curved edges or to achieve a more robust connection with the clamping wall 441 of the liquid storage container 1. These surface treatment processes can include metal grinding, spraying, spray sandblasting, polishing, or coating. In another embodiment, as shown in FIG. 17, on the inside of the chamber, the clamping wall 441 is flush with the heating plate 44 at the connection area. In another embodiment, as depicted in FIG. 26, the connection between the heating plate 44 and the clamping wall 441 is flat (there is no height difference structure 47). The structure can add surface treatment methods such as a spraying process (covering the connection point between the heating plate 44 and the clamping wall 441 with a waterproof material to form a waterproof film) in case of leakage. To ensure a stable connection between the heating plate 44 and the wall 41 of the bottom part 4, as well as effective heat conduction, the width of the clamping wall 441 is at least 0.3 mm. The contact area (where the heating plate 44 is embedded into the wall 41 of the bottom part 4) between the wall 41 of the bottom part 4 and the heating plate 44 is not less than 66 $mm^2$. (The heating plate 44 must be embedded at least 0.3 mm in width to ensure a stable and firm connection with the bottom part 4, preventing detachment. To ensure that the heating plate 44 can heat the liquid, such as water, inside the liquid storage 1, the area of the heating plate 44 should be at least 3100 $mm^2$.) Additionally, the thickness of the heating plate 44 does not exceed 1 mm, and its total surface area is no more than 16000 $mm^2$. To reduce the rate of product defects (leaks, cracks or other production problems), as shown in FIG. 25, the portion of the heating plate 44 embedded into the clamping wall 441 features at least one height difference structure 47 in an arc shape with a minimum being 0.3 mm. Setting the height difference is to lengthen the path through which liquid in the liquid storage container would flow outward. Seeing the path as a cylindrical tube, through the fluid dynamics formula, the volumetric flow rate Q per second through the pipe $Q=(\pi\Delta Pr^4)/8\mu L$ (where $\Delta P$ is the pressure difference at the ends of the pipe, it is known that r is the radius of the cylindrical tube, u is the dynamic viscosity of the fluid, and L is the length of the pipe). Given that the radius of the cylindrical tube and the dynamic viscosity of the fluid remain constant, when the pressure inside liquid storage container 1 is constant, the pressure difference equals the internal pressure minus the external pressure (i.e., atmospheric pressure). The longer the pipe through which the liquid flows, the smaller the flow rate Q. This means that lengthening the path through which the liquid in the liquid storage container flows outward can prevent water inside the bottom part 4 from leaking out. Therefore, adding a height difference structure on the heating plate 44 can effectively extend the length L of the pipe. However, if the extension is too short, it will not be effective. The minimum height difference structure should be 0.3 mm. The material of the heating plate 44 can be stainless steel, aluminum alloy, ceramic coating, etc. Typically, stainless steel is used because the stainless steel has corrosion resistance and durability. Stainless steel can withstand the erosion of water, steam, acids, alkalis, and many other chemical substances. The heating plate is parallel to the horizontal plane and flush with the lowest point of the bottom part 4, ensuring the overall stability of the liquid storage container 1.

In another embodiment, the connection method between the heating plate and the wall 41 of the bottom part 4 can also be ultrasonic connection, welding, or other connection methods that do not require the addition of extra materials.

In another embodiment, the top cover can be without a platform, and the structures of the upper sealing element 321 and lower sealing elements 322 of the middle layer are symmetrically identical. A perimeter of the outer edge of the upper sealing element 321 conforms to the inner wall of the top cover 2 to create a seal with the top cover 2, while the perimeter of the outer edge of the lower sealing element 322 fits against the inner wall of the bottom part 4 to form a seal with the bottom part 4. Specifically, the perimeter of the upper sealing element 321 is slightly larger than the perimeter of the inner edge of the wall 21 of the top cover 2 of the liquid storage container 1. The perimeter of the lower sealing element 322 is slightly larger than the perimeter of the inner edge of the wall 41 of the bottom part 4 of the liquid storage container 1. Both can rely on the properties of their materials to deform and seal the openings upon connection, forming a tight anti-spill ring.

Embodiment 2

Figure 19:
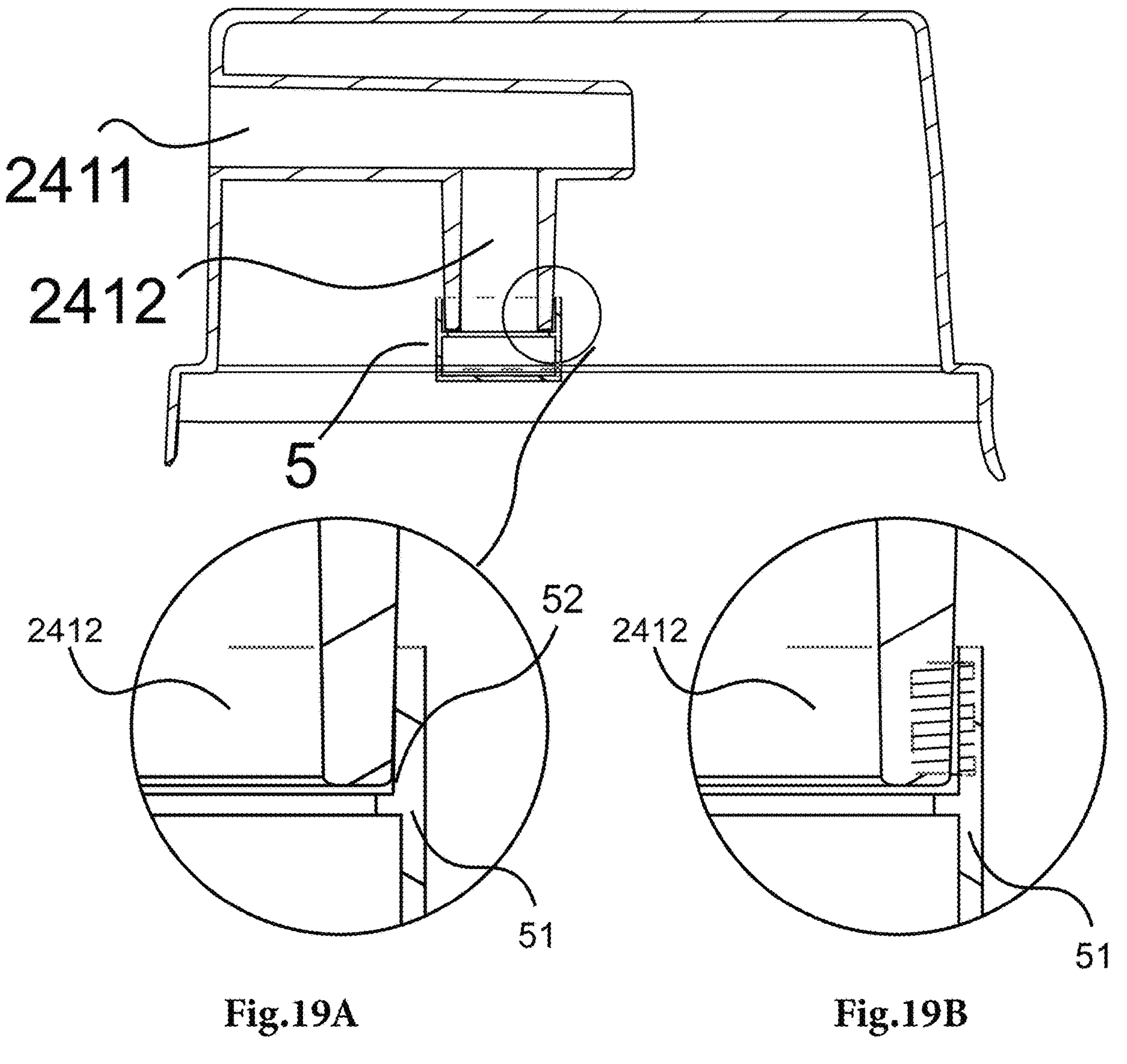
FIGS. 19A and 19B are schematic diagrams of the connection between the intake port of the top cover and the diverter of a liquid storage container in accordance with an embodiment.
Figure 20:
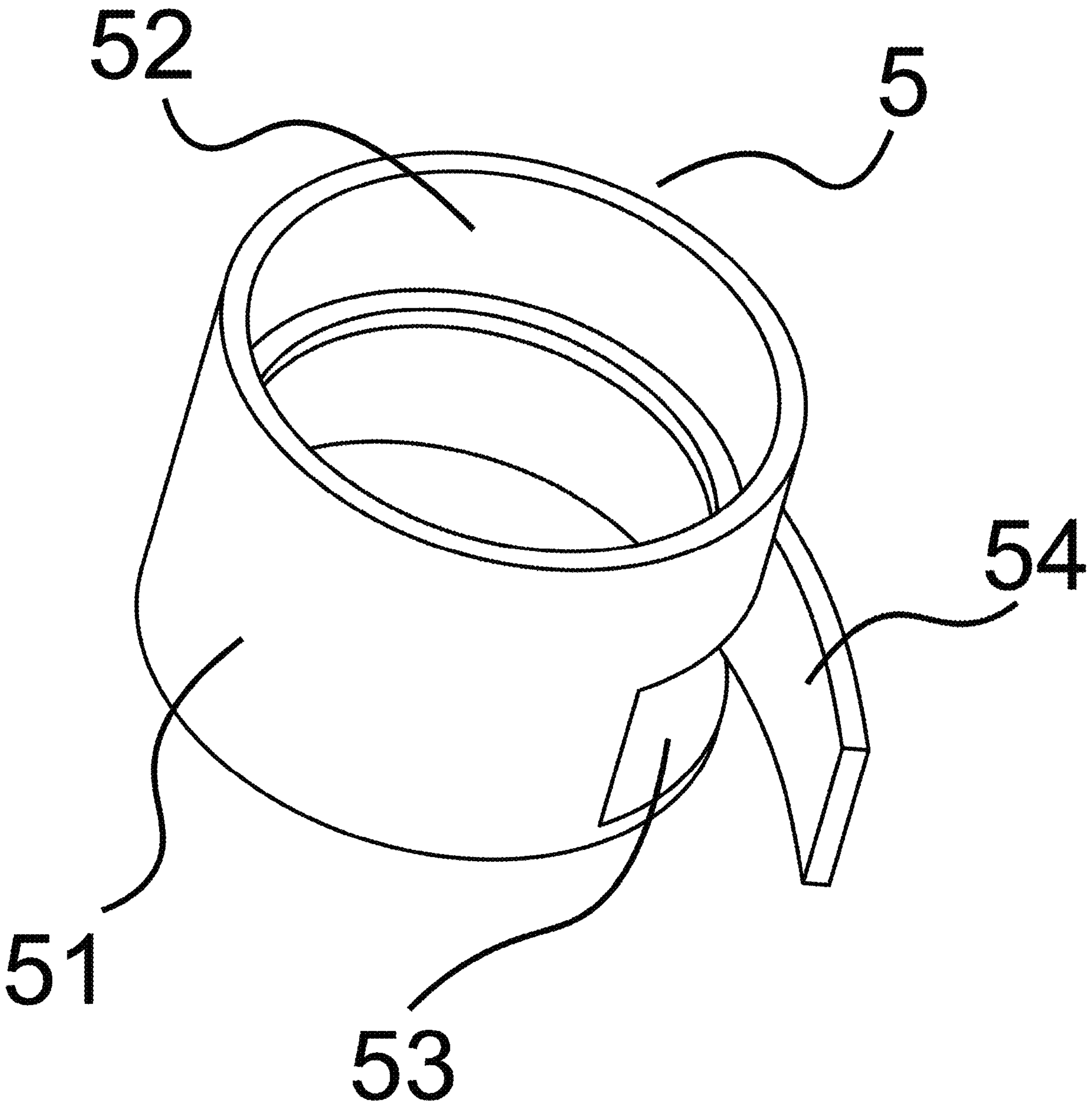
FIG. 20 is a schematic diagram of the structure of the diverter in accordance with an embodiment.

In this embodiment, a liquid storage container 1, used to moisten pressurized breathable gas delivered to a patient, can provide heat to the liquid stored within the chamber when connected to an airflow generator in a working position. The liquid storage container 1 includes a top cover 2, a middle layer 3, and a bottom part 4. The liquid storage container 1 is divided into a front end and a rear end, with the top cover 2, the middle layer 3, and the bottom part 4 each having corresponding front and rear ends. The liquid storage container provided in this embodiment differs from the liquid storage container 1 in embodiment 1 in that the second section 2412 of the intake port 23 is connected to a diverter 5. As shown in FIGS. 19 and 20, the pipes extending from the intake port 23 and the exhaust port 24 are parallel to each other. The intake port 23 includes a first section 2411 and a second section 2412, which are not parallel. The second section 2412 extends towards the bottom part 4 and is perpendicular to the horizontal plane. It can be connected to the diverter 5, which is used to change the direction of the airflow. The maximum extent to which the second section 2412 extends downward can be flush with the end surface of the first opening 22 of the top cover 2. The diverter 5 is cylindrical in shape, with an overall height at or between 10 to 50 mm. One end has an interface 52 for connection to the second section 2412, while the other end is closed to prevent airflow from directly blowing towards the water surface and causing splashing. The diverter 5 also includes walls 51 that connect both ends and have an opening 53. Pressurized airflow exits through the opening 53, thereby changing the direction of the airflow towards the water surface. A baffle 54 of a certain length can extend from the opening 53. The diverter 5 can be made from one or more materials such as polyethylene, polypropylene, polycarbonate, silicone, rubber, etc. The connection between diverter 5 and the second section 2412 can be achieved through material deformation (such as snap-fits or soft rubber friction connections, as shown in FIG. 19A), mechanical connections like magnetic attraction, or not detachable connections such as ultrasonic bonding (as shown in FIG. 19B).

Embodiment 3

Figure 21A:
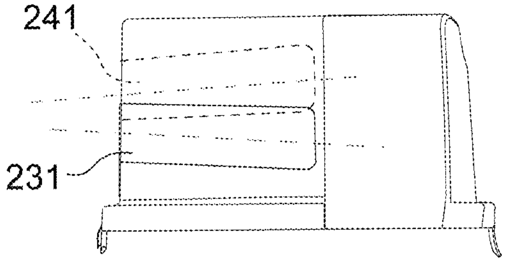
FIGS. 21A and 21B are schematic diagrams of the structure of the pipes that extend from the uniform intake port and exhaust port of the top cover of the liquid storage container in accordance with an embodiment, which are parallel in a horizontal plane.
Figure 21B:
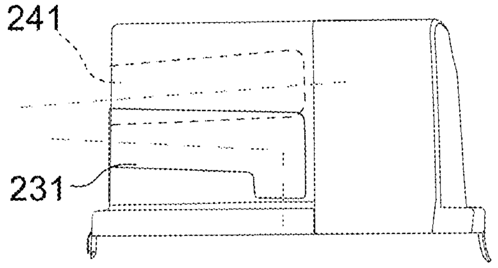
Figure 22A:
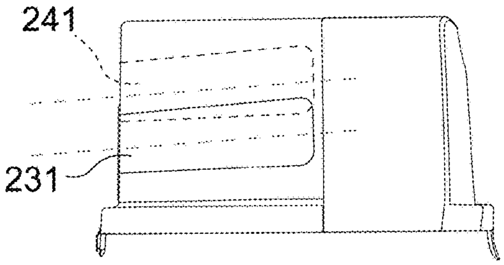
FIGS. 22A and 22B are schematic diagrams of the structure of another form of pipes that extend from the uniform intake port and exhaust port of the top cover of a liquid storage container in accordance with an embodiment.

In this embodiment, a liquid storage container 1, used to moisten pressurized breathable gas delivered to a patient, can provide heat to the liquid stored within the chamber when connected to an airflow generator in a working position. The liquid storage container 1 includes a top cover 2, a middle layer 3, and a bottom part 4. The liquid storage container 1 is divided into a front end and a rear end, with the top cover 2, the middle layer 3, and the bottom part 4 each having corresponding front and rear ends. In this embodiment, the liquid storage container provided in this embodiment differs from the liquid storage container 1 in embodiment 1 in that the pipes extending from the intake port 23 and the exhaust port 24 are not parallel. As shown in FIGS. 21A and 21B, specifically, the pipes extending from the exhaust port 24 and the intake port 23 are uniform, and their axes are parallel in the horizontal plane but not parallel in the plane perpendicular to the horizontal plane. 1) The pipe extending from the intake port 23 can slightly incline towards the rear end of the liquid storage container 1. This design helps prevent the backflow of air containing water vapor into the interior of the machine. 2) The intake port 23 includes a first section 2411 and a second section 2412, which are not parallel to each other. The second section extends towards the bottom part 4 and is perpendicular to the horizontal plane. As shown in FIG. 22A, specifically, the pipes extending from the exhaust port 24 and the intake port 23 are uniform, but their axes are not parallel in the horizontal plane and are parallel in the plane perpendicular to the horizontal plane. The pipes may or may not intersect each other.

Figure 22B:
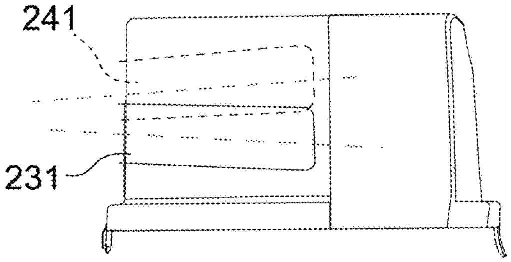

In another embodiment, as shown in FIG. 22B, specifically, the pipes extending from the exhaust port 24 and the intake port 23 are uniform, but their axes are neither parallel in the horizontal plane nor in the plane perpendicular to the horizontal plane.

Figure 23A:
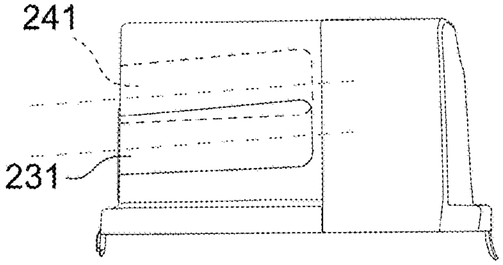
FIGS. 23A and 23B are schematic diagrams of the structure of the pipes that extend from the intake port and exhaust port of the top cover of a liquid storage container in accordance with an embodiment.
Figure 23B:
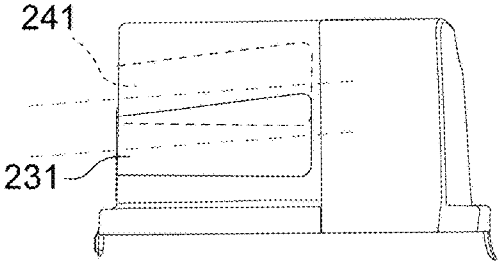

In another embodiment, as illustrated in FIGS. 23A and 23B, specifically, the pipes extending from the intake port 23 and the exhaust port 24 can also have shapes and/or diameters, e.g., vary non-uniformly along a length of the pipe 231 and pipe 241.

Furthermore, it is possible to combine the technical features from the above embodiments as needed to obtain a liquid storage container 1 that includes all or some of these technical features.

Implementing the liquid storage container in the disclosure provides at least the following beneficial effects:

1. The separable structure on a flat plane is easier to install and use: Most liquid storage containers on the market have their top cover and bottom part connected by hinges. The advantage of hinge connections is that they can ensure the integration of the liquid storage container, thus preventing the loss of parts. Hinge connections can be categorized into non-detachable and detachable types. a. Non-detachable hinge connections, while ensuring the integration of the liquid storage container, have the situation of an unreasonable hinge design. The top cover of the liquid storage container cannot be completely laid flat and can only hang in the air via the hinge, which can lead to uneven force distribution and flip the liquid storage container over, or cause it to close while it is filling with water. The former may result in the spilling of water from the liquid storage container, and the latter may lead the patient's fingers to get pinched. b. The removable hinge, due to its mechanical structure, cannot be easily detached and there is a risk of damage at the hinge of the top cover during the disassembly process: due to structural requirements of the hinge, there are certain gaps at the connection area, which can easily accumulate dirt and are difficult to clean. The sealing element within the liquid storage container requires contact and compression with the platform of the upper and lower covers of the liquid storage container to form a seal, and the platform area must be sufficient to achieve a good seal. Most liquid storage containers on the market have the platform of the lower cover directly at the opening of the lower cover, which, during production, blocks the direct output of the product, thereby increasing production costs. The connection structure of the top cover and bottom part inside the liquid storage container is configured as a simple removable connection, and the connection between the sealing element and the platform is redesigned. The liquid storage container is divided into three parts: the top cover, the middle layer, and the bottom part. This simplifies the complex structure of the components, allowing the three parts to be more easily demolded in production without the obstruction of platforms or protrusions. The components are connected through simple mechanical means: a. The connection between the top cover and the bottom part is made using a protruding snap-fit form connection, which avoids the issue of non-removable hinges: b. The middle layer includes a sealing element and a stopping element, both produced by an integrated molding process. The stopping element of the middle layer comes into contact with the direct open end surface of the bottom part, forming a platform that limits the movement of the sealing element. The connection areas of the three components are all configured to be flat and, through a simple connection design, solving the following problems: a. The difficulties of the liquid storage container's lower cover in production are solved: b. It allows for a simple connection or disassembly of the top covers and lower covers. c. Installing the middle layer directly on the bottom part with a flat surface is easier to operate, compared to installing the sealing element on the top cover that is fixed by hinges, improving user-friendliness: d. The open end surface of the bottom part being flat, as opposed to non-flat, makes patients less prone to misjudge the water level. e. The connection between the top cover and the bottom part being fully detachable does not hinder the patient from adding water due to the presence of the top cover.

2. The structural design of the middle layer: In ordinary liquid storage containers, the seal is fixedly connected to the top cover, and then comes into contact with the platform of the bottom part to form a seal. This connection method requires the patient to ensure that the top cover and the seal are tightly connected: otherwise, it is very likely that the sealing element will fall off when the top cover is being fastened clockwise. Some liquid storage containers are manufactured with sealing elements using an integrally formed method. This type of connection usually makes the sealing elements difficult to replace and results in high maintenance or replacement costs. The choice of sealing material also needs to be based on the characteristics of the liquid storage container material, which narrows the range of options. Combining the platform that restricts the sealing element with the ordinary sealing element not only optimizes the production of the components but also provides double assurance for the gas and liquid seals of the entire liquid storage container. The middle layer includes a stopping element, an upper sealing element, and a lower sealing element. The stopping element has at least a part of its perimeter of the outer edge that is not smaller than a perimeter of an inner edge of the second opening of the bottom part, which is used to prevent the middle layer from descending. The upper seal includes support arms of a certain height and extended thin sheets. There is a certain gap between the thin sheets and the stopping element to facilitate the deformation of the upper sealing element when it contacts the platform of the top cover. The perimeter of the outer edge of the lower sealing element is slightly larger than the perimeter of the inner edge of the wall of the bottom part of the liquid storage container. It can rely on its own material characteristics to deform during connection, sealing the opening of the bottom part, and forming a tight anti-overflow ring.

3. The heating plate and the bottom part are integrally formed and connected to the wall. Heating plates are commonly connected to the wall of the bottom part with materials such as silicone or rubber. However, materials like silicone and rubber are prone to deformation and aging due to continuous exposure to high temperatures, which can consequently reduce the sealing ability of the liquid storage container. Therefore, the heating plate is integrally formed with the wall of the bottom part of the liquid storage container through a molding connection, which can effectively reduce the separated seams or connection points, provide higher structural strength and stability, reduce the risk of leakage, and due to the reduction of excess processes, improve production and inspection efficiency, save time and labor costs, and reduce the defect rate of the products.

4. Environmentally Friendly: Combining the above three points, the redesign of the liquid storage container significantly reduces unnecessary waste of resources, both in terms of production, manufacturing, and material selection. This makes the overall production process simpler and uses fewer materials while still ensuring air-tightness. The conservation of resources during the production process helps to reduce the emission of greenhouse gases, thereby alleviating the pressure of climate change, reducing the exploitation of natural resources, and lessening the damage to the natural environment, establishing a healthier and more sustainable future.

The various technical features of the embodiments mentioned above can be combined in any manner. To keep the description concise, not all possible combinations of technical features in these embodiments have been described. However, as long as there is no contradiction in the combination of these technical features, they should be considered to be within the scope disclosed in this specification.

It should be noted that the above-mentioned embodiments only represent several ways of implementing the disclosure. While the descriptions are relatively specific and detailed, the information provided in the document does not imply a limitation on the scope of the patent. It should be pointed out that, for those skilled in the field of face mask assembly, various modifications and improvements can be made without departing from the basic concept of the disclosure, which are all within the scope of protection of the disclosure. Therefore, the scope of protection of the patent for the disclosure should be determined by the appended claims.

It must be noted that as used herein and in the appended claims, the singular forms “a”, “an”, and “the” include their plural equivalents, unless the context clearly dictates otherwise.

The invention claimed is:

1. A liquid storage container to moisten pressurized breathable gas delivered to airways, wherein when the liquid storage container and an airflow generator are in an operational position, the liquid storage container supplies heat to liquid within a chamber, wherein the liquid storage container comprises:

- a bottom part including an opening that fits with a top cover, at least one receiving part at a front end of the bottom part to engage with the top cover, and at least one receiving part at a rear end of the bottom part to connect to the top cover, and wherein the bottom part includes an integrally formed wall and a heating plate;
- wherein the heating plate is configured to conduct heat, integrally formed with the wall of the bottom part together to form the chamber to contain the liquid, with a minimum capacity of the chamber being 150 mL;
- wherein the wall of the bottom part has a clamping wall at a connection point with the heating plate, and
- wherein a portion of the heating plate is embedded in the clamping wall such that an entry point of the heating plate into the clamping wall is lower than a height difference structure of the heating plate embedded in the clamping wall and an area of the portion of the heating plate embedded into the wall of the bottom part is not less than 66 $mm^2$.

2. The liquid storage container according to claim 1, wherein the heating plate comprises edges with curves, and wherein the edges with curves are obtained through a surface treatment process that includes metal grinding, spraying, spray sandblasting, polishing, or coating.

3. The liquid storage container according to claim 1, wherein the bottom part further comprises corresponding steps to guide the liquid storage container into the airflow generator.

4. A liquid storage container to moisten pressurized breathable gas delivered to airways, wherein when the liquid storage container and an airflow generator are in operational position, the liquid storage container supplies heat to liquid within a chamber, wherein the liquid storage container comprises:

- a bottom part including an opening that fits with a top cover, at least one receiving part at a front end of the bottom part to engage with the top cover, and at least one receiving part at a rear end of the bottom part to connect to the top cover, and wherein the bottom part includes an integrally formed wall and a heating plate;
- wherein the heating plate is configured to conduct heat, integrally formed with the wall of the bottom part together to form the chamber to contain the liquid;
- wherein the wall of the bottom part has a clamping wall at a connection point with the heating plate, and
- wherein a portion of the heating plate is embedded in the clamping wall such that an entry point of the heating plate into the clamping wall is lower than a height difference structure of the heating plate embedded in the clamping wall, and the height difference structure has a height of not less than 0.3 mm to prevent liquid inside the chamber from leaking to an exterior of the chamber.

5. The liquid storage container according to claim 4, wherein the heating plate comprises edges with curves, wherein the edges with the curves are obtained through a surface treatment process that includes metal grinding, spraying, spray sandblasting, polishing, or coating.

6. The liquid storage container according to claim 4, wherein the height difference structure embedded in the clamping wall has an arc shape.

7. The liquid storage container according to claim 4, wherein the bottom part includes a locator for the top cover, which has a form of a protrusion, a groove, a magnet or a contour.

8. The liquid storage container according to claim 4, wherein the bottom part further comprises corresponding steps to guide the liquid storage container into the airflow generator.

9. A liquid storage container to moisten pressurized breathable gas delivered to airways, wherein when the liquid storage container and an airflow generator are in an operational position, the liquid storage container supplies heat to liquid within a chamber, wherein the liquid storage container comprises:

- a bottom part including an opening that fits with a top cover, at least one receiving part at a front end of the bottom part to engage with the top cover, at least one receiving part at a rear end of the bottom part to connect to the top cover, an integrally formed wall, and a heating plate;
- wherein the heating plate is configured to conduct heat, integrally formed with the wall of the bottom part together to form the chamber to contain the liquid;
- wherein the wall of the bottom part has a clamping wall at a connection point with the heating plate, and a portion of the heating plate is embedded in the clamping wall such that an entry point of the heating plate into the clamping wall is lower than a height difference structure of the heating plate embedded in the clamping wall; and
- wherein a thickness of the heating plate does not exceed 1 mm, and an area of the heating plate is at least 3100 $mm^2$.

10. The liquid storage container according to claim 9, wherein a minimum capacity of the chamber is 150 mL.

11. The liquid storage container according to claim 9, wherein an area of the heating plate embedded into the wall of the bottom part is not less than 66 $mm^2$.

12. A liquid storage container to moisten pressurized breathable gas delivered to airways, wherein when the liquid storage container and an airflow generator are in an operational position, the liquid storage container supplies heat to liquid within a chamber, wherein the liquid storage container comprises:

a bottom part including an opening that fits with a top cover, at least one receiving part at a front end of the bottom part to engage with the top cover, at least one receiving part at a rear end of the bottom part to connect to the top cover, an integrally formed wall, and a heating plate;

wherein the heating plate is configured to conduct heat, integrally formed with the wall of the bottom part together to form the chamber to contain the liquid;

wherein the wall of the bottom part has a clamping wall at a connection point with the heating plate, wherein a portion of the heating plate is embedded in the clamping wall such that an entry point of the heating plate into the clamping wall is lower than a height difference structure of the heating plate embedded in the clamping wall, and wherein a width of the clamping wall is at least 0.3 mm.

13. The liquid storage container according to claim 12, wherein a total area of the heating plate does not exceed 16000 $mm^2$.

14. The liquid storage container according to claim 12, wherein the height difference structure embedded in the clamping wall is not less than a height of 0.3 mm.

15. The liquid storage container according to claim 12, wherein the heating plate is flush with a lowest point of the bottom part.

16. The liquid storage container according to claim 12, wherein height difference structure embedded in the clamping wall has an arc shape.

* * * * *